(12) United States Patent
Gunn et al.

(10) Patent No.: US 10,893,895 B2
(45) Date of Patent: Jan. 19, 2021

(54) MINIMALLY INVASIVE SCREW EXTENSION ASSEMBLY

(71) Applicant: Amendia, Inc., Marietta, GA (US)

(72) Inventors: Joshua David Gunn, Woodstock, GA (US); David Brett Cain, Marietta, GA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 16/051,670

(22) Filed: Aug. 1, 2018

(65) Prior Publication Data

US 2018/0338781 A1 Nov. 29, 2018

Related U.S. Application Data

(62) Division of application No. 15/236,036, filed on Aug. 12, 2016, now Pat. No. 10,064,662.

(51) Int. Cl.
*A61B 17/70* (2006.01)
*A61B 17/00* (2006.01)
*A61B 17/86* (2006.01)

(52) U.S. Cl.
CPC ...... *A61B 17/708* (2013.01); *A61B 17/00234* (2013.01); *A61B 17/7086* (2013.01); *A61B 17/8665* (2013.01); *A61B 17/7085* (2013.01)

(58) Field of Classification Search
CPC .......................... A61B 17/708; A61B 17/7086
See application file for complete search history.

(56) References Cited

U.S. PATENT DOCUMENTS

| 7,179,261 | B2 | 2/2007 | Sicvol et al. |
| 7,651,502 | B2 | 1/2010 | Jackson |
| 7,666,189 | B2 | 2/2010 | Gerber et al. |
| 8,142,437 | B2 | 3/2012 | Mclean et al. |
| 8,167,887 | B2 | 5/2012 | Mclean et al. |
| 8,394,108 | B2 | 3/2013 | Mclean et al. |
| 8,439,922 | B1 | 5/2013 | Arnold |
| 8,512,383 | B2 | 8/2013 | Mclean et al. |
| 8,535,318 | B2 | 9/2013 | Peterson et al. |
| 8,777,954 | B2 | 7/2014 | Mclean et al. |
| 8,790,348 | B2 | 7/2014 | Stad et al. |
| 8,845,640 | B2 | 9/2014 | Mclean et al. |
| 9,050,139 | B2 | 6/2015 | Jackson |
| 9,078,709 | B2 | 7/2015 | Mcbride |
| 9,101,416 | B2 | 8/2015 | Dunbar et al. |
| 9,510,875 | B2 * | 12/2016 | Reitblat ............... A61B 17/708 |
| 9,642,654 | B2 | 5/2017 | Reimels |

(Continued)

*Primary Examiner* — Julianna N Harvey

(57) ABSTRACT

A screw extension assembly for use in minimally invasive spinal surgery, the assembly has an inner slotted shaft and an outer shaft, a rod reducer and a removable nut. The combination when assembled is configured to move a spinal fixation rod into a slotted rod receiving spinal implant where it is seated and affixed thereto. The screw extension assembly further has a locking knob rotationally coupled to a proximal end of the outer shaft, wherein the inner shaft has one or more cam grooves and the locking knob has a pin extending into and guided by said cam groove causing the outer shaft to translate longitudinally upon rotation of the locking knob relative to the inner shaft toward an engaged position locking the deflectable legs in the coupled position to the slotted rod receiving implant.

10 Claims, 24 Drawing Sheets

(56) References Cited

U.S. PATENT DOCUMENTS

| | | | |
|---|---|---|---|
| 10,064,662 B2* | 9/2018 | Gunn | A61B 17/00234 |
| 10,368,923 B2* | 8/2019 | Altarac | A61B 17/7085 |
| 2004/0147937 A1* | 7/2004 | Dunbar, Jr. | A61B 17/7091 |
| | | | 606/99 |
| 2005/0131408 A1* | 6/2005 | Sicvol | A61B 17/7032 |
| | | | 606/86 A |
| 2006/0036255 A1 | 2/2006 | Pond et al. | |
| 2006/0074418 A1* | 4/2006 | Jackson | A61B 17/7086 |
| | | | 606/914 |
| 2006/0111712 A1* | 5/2006 | Jackson | A61B 17/7037 |
| | | | 606/914 |
| 2012/0022594 A1* | 1/2012 | Walker | A61B 17/708 |
| | | | 606/264 |
| 2012/0191144 A1* | 7/2012 | Peultier | A61B 17/7086 |
| | | | 606/86 A |
| 2013/0060294 A1* | 3/2013 | Donahue | A61B 17/8605 |
| | | | 606/308 |
| 2013/0103094 A1* | 4/2013 | Beale | A61B 17/7076 |
| | | | 606/279 |
| 2013/0245702 A1* | 9/2013 | McBride | A61B 17/7076 |
| | | | 606/305 |
| 2014/0052187 A1* | 2/2014 | McBride | A61B 17/708 |
| | | | 606/264 |
| 2014/0052197 A1* | 2/2014 | McBride | A61B 17/7085 |
| | | | 606/86 A |
| 2014/0277137 A1* | 9/2014 | Stad | A61B 17/7076 |
| | | | 606/246 |
| 2014/0277206 A1* | 9/2014 | Reitblat | A61B 17/708 |
| | | | 606/86 A |
| 2015/0012049 A1 | 1/2015 | Mclean et al. | |
| 2015/0039035 A1* | 2/2015 | Kruger | A61B 17/7037 |
| | | | 606/264 |
| 2015/0066042 A1 | 3/2015 | Cummins | |
| 2015/0182265 A1 | 7/2015 | Biedermann et al. | |
| 2015/0359571 A1 | 12/2015 | Biedermann et al. | |
| 2016/0089188 A1* | 3/2016 | McBride, Jr. | A61B 17/7076 |
| | | | 606/279 |
| 2016/0113682 A1* | 4/2016 | Altarac | A61B 17/7085 |
| | | | 606/265 |
| 2017/0164980 A1* | 6/2017 | Le Roux | A61B 17/7076 |
| 2018/0008318 A1* | 1/2018 | Fiechter | A61B 17/7076 |
| 2018/0042645 A1* | 2/2018 | Gunn | A61B 17/00234 |
| 2019/0142471 A1* | 5/2019 | Lindner | A61B 17/7037 |
| | | | 606/266 |

* cited by examiner

MINIMALLY INVASIVE SCREW EXTENSION ASSEMBLY

RELATED APPLICATIONS

The present invention is a division of co-pending U.S. application Ser. No. 15/236,036 filed Aug. 12, 2016 entitled "Minimally Invasive Screw Extension Assembly".

TECHNICAL FIELD

The present invention relates to a minimally invasive screw extension assembly for seating a fixation rod into a spinal fixation rod receiving implant and securing the seated fixation rod as part of a vertebral corrective surgery.

BACKGROUND OF THE INVENTION

Spinal surgeons are required to implant a variety of rods, screws and plates into the bony skeletal structure of the spine to correct a variety of misalignments and repair damage that exist between the vertebral bodies. A particularly useful procedure involves the placement of rod receiving spinal implants with pedicle screws into the vertebrae. These rod receiving implants commonly have a slotted "U" shaped body with a pedicle screw extending from the base of the slotted body. When the surgeon implants these devices in the bones along the portion of the spine to be corrected, he must then connect two or more of these implants using fixation rods. The fixation rods are typically solid round cylindrical metal devices that can be straight or curved. The rods must be driven inwardly to be seated to fit between the "U" shaped slotted body. Once in a seated position, the rod can be fixed rigidly into the rod receiving implant by tightening a set screw into the threaded legs of the slotted body clamping the fixation rod securely to the slotted body.

One difficulty for the surgeon is aligning the fixation rods with the slotted rod receiving implants and moving the rod inwardly toward the slot. This is particularly difficult when the implants need to be positioned to correct a preexisting misalignment. This aspect of positioning the rod is called reduction or reducing and a variety of elongated tools have been developed to facilitate the proper placement of fixation rods.

The present invention, as described hereinafter, is an improved tool assembly that can easily be clipped onto a rod receiving spinal implant and reduce a fixation rod, and while clipped in place, deliver a set screw to fix the rod in a proper position to achieve the corrective spinal alignment and support for the particular surgery.

These and other objectives are achieved by the invention as described hereinafter.

SUMMARY OF THE INVENTION

A screw extension assembly for use in minimally invasive spinal surgery, the assembly has an inner slotted shaft and an outer shaft, a rod reducer and a removable nut. The combination when assembled is configured to move a spinal fixation rod into a slotted rod receiving spinal implant where it is seated and affixed thereto. The inner slotted shaft is an elongated hollow tubular shaft having a proximal end, a distal end and a slotted distal end portion having a pair of slots open through the distal end and defining a pair of deflectable leg extensions. Each leg extension has a projection configured to engage a groove on an outer surface of a slotted rod receiving implant thereby coupling the inner shaft to the slotted rod receiving implant adjacent slots at the distal end of the leg extensions having a plurality longitudinal edges keyed to abut proximal walls of the slotted rod receiving implant to prevent rotation. The outer shaft is configured to receive and pass over the inner shaft. The outer shaft has a pair of slots open through a distal end with longitudinal rails adjacent edges of each slot of the outer shaft to slide along each edge of the slots of the leg extensions of the inner shaft along at least a portion of the slots. The outer shaft when moved inwardly toward the distal end of the inner shaft into an engaged position locks the deflectable leg extensions in a coupled position to the grooves of the slotted rod receiving implant. The outer shaft at the distal end has two or more prongs extending from the distal end, the two or more prongs when the outer shaft is moved engages an inner side of the slotted rod receiving implant in the engaged position.

A proximal portion adjacent the proximal end of the inner shaft has a threaded portion wherein the threads of the threaded portion have longitudinal extending grooves aligned to receive the longitudinal rails of the outer shaft. The grooves are aligned with the edges of the slots forming a keyed pathway allowing the longitudinal rails to slide relative to the inner shaft toward the distal end on assembly.

The screw extension assembly further has a locking knob rotationally coupled to a proximal end of the outer shaft, wherein the inner shaft has one or more cam grooves and the locking knob has a pin extending into and guided by said cam groove causing the outer shaft to translate longitudinally upon rotation of the locking knob relative to the inner shaft toward an engaged position locking the deflectable legs in the coupled position to the slotted rod receiving implant. The one or more cam grooves has a cam over pocket feature in a distal end of the cam groove, the cam over pocket locks the locking knob at or past the engaged position. The cam over pocket at the distal end of the cam groove rotationally moves the locking knob in the absence of forward longitudinal translation of the outer shaft to the inner shaft at the locked position.

On assembly of the inner and outer shafts, the pair of slots in the inner shaft and the pair of slots in the outer shaft are aligned to pass rods therethrough. The screw extension assembly further has the rod reducer. The rod reducer is a hollow tube with a distal end to push a rod received in the aligned slots of the assembly when the rod reducer is placed over the inner and outer shaft. The screw extension assembly further has the nut. The nut has female threads for engaging the threaded proximal end of the inner shaft and wherein the nut when tightened abuts a proximal end of the reducer and pushes the reducer inwardly to move a rod received in the aligned slots of the assembly into the slotted rod receiving implant.

In one embodiment, the threads of the proximal end of the inner shaft has a pitch sufficient to allow the nut to auto-rotate, solely due to the weight of the nut, to abut the proximal end of the reducer and further rotation pushes the reducer inwardly to seat a rod in a rod seating position. The nut is preferably removable and separate from the outer shaft, this allows the rod reducer to fit easily over the assembled inner and outer shafts. The outer shaft has flats in the proximal portion and the locking knob has flats configured to align with the flats of the outer shaft when the locking knob is rotated to a locked position allowing the reducer with complimentary internal flats to non-rotationally move relative to the assembly as the nut pushes the reducer.

A kit for use in minimally invasive spinal surgery can be assembled using these components. The kit would have a slotted rod receiving implant, the rod receiving implant having a proximal slotted rod holding element and a threaded bone fastener extending distal from the rod holding element; an inner slotted shaft, the inner slotted shaft being an elongated hollow tubular shaft having a proximal end, a distal end and a slotted distal end portion having a pair of slots open through the distal end defining a pair of deflectable leg extensions, each leg extension having a projection configured to engage a groove on an outer surface of the slotted rod receiving implant thereby coupling the inner shaft to the slotted rod receiving implant adjacent slots at the distal end of the leg extensions having a plurality longitudinal edges keyed to abut proximal walls of the slotted rod receiving implant to prevent rotation; an outer shaft configured to receive and pass over the inner shaft; the outer shaft having a pair of slots open through a distal end with longitudinal rails adjacent edges of each slot of the outer shaft to slide along each edge of the slots of the leg extensions of the inner shaft along at least a portion of the slots; and wherein the outer shaft when moved inwardly relative to translate toward the distal end of the inner shaft into an engaged position locks the deflectable legs in a coupled position to the grooves of the slotted rod receiving implant.

The kit may further include a threaded set screw for attachment to internal threads of the rod holding element configured to hold a rod when tightened and a fastener driver tool to pass through the inner shaft to fasten and tighten the set screw; a rod reducer, the rod reducer having a distal end for pushing a rod and an opposing proximal end. A proximal portion adjacent the proximal end of the inner shaft has a threaded portion and the kit further may include a nut for engaging the threads of the proximal end of the inner shaft and to abut at the proximal end of the rod reducer, the handle when tightened pushes a rod into a seated position in the rod receiving element.

The kit further may include a locking knob rotationally coupled to a proximal end of the outer shaft wherein the inner shaft has one or more cam grooves and the locking knob is pinned to said cam groove causing the outer shaft to translate longitudinally upon rotation of the locking knob relative to the inner shaft toward an engaged position locking the deflectable legs in the coupled position to the slotted rod receiving implant, wherein the one or more cam grooves has a cam over pocket feature in an end of the cam groove, the cam over pocket locks the locking knob at or past the engaged position and wherein the cam over pocket at the end of the cam groove rotationally moves the locking knob in the absence of forward longitudinal translation of the outer shaft to the inner shaft at the locked position.

The kit wherein the inner shaft and outer shaft have aligned slots to pass rods therethrough. The kit further has a nut having female threads for engaging the threaded proximal end of the inner shaft and wherein the nut when tightened pushes the reducer inwardly to move a rod into the slotted rod receiving implant wherein the nut is removable and separate from the outer shaft wherein the threads of the proximal end of the inner shaft have a pitch sufficient to allow the nut to auto-rotate, solely due to the weight of the nut, to abut the proximal end of the reducer and further rotation pushes the reducer inwardly to a rod seating position. The kit wherein the outer shaft has flats in the proximal portion and the locking knob has flats configured to align with the flats of the outer shaft when the locking knob is rotated to a locked position allowing the reducer with complimentary internal flats to non-rotationally move relative to the assembly as the nut pushes the reducer.

BRIEF DESCRIPTION OF THE DRAWINGS

The invention will be described by way of example and with reference to the accompanying drawings in which.

DETAILED DESCRIPTION OF THE INVENTION

Figure 1:
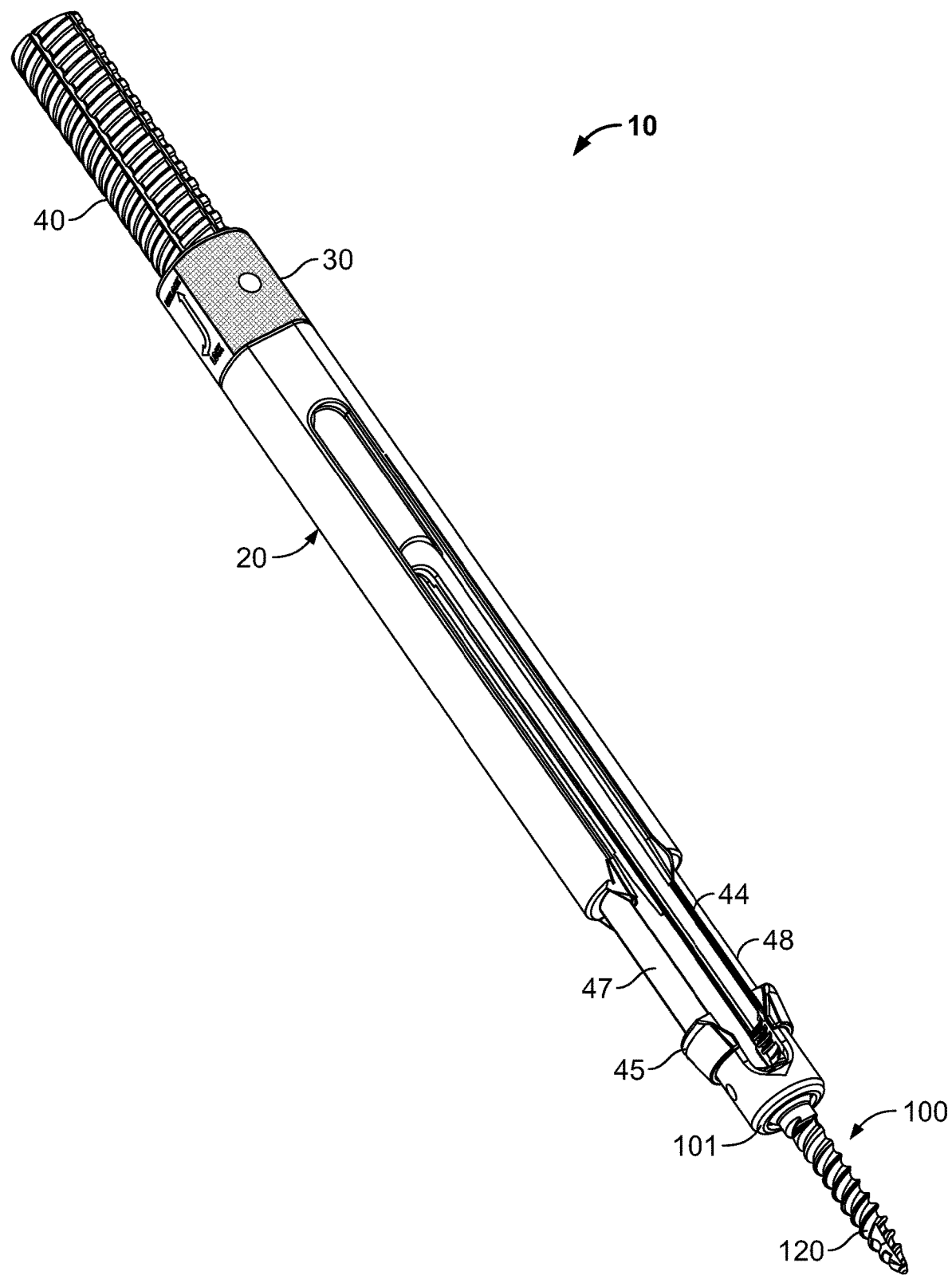
FIG. 1 is a perspective view of the screw extension assembly of the present invention showing the deflectable leg extensions of the inner slotted shaft attached to a slotted rod receiving implant with the outer shaft not yet in the locked position.
Figure 1A:
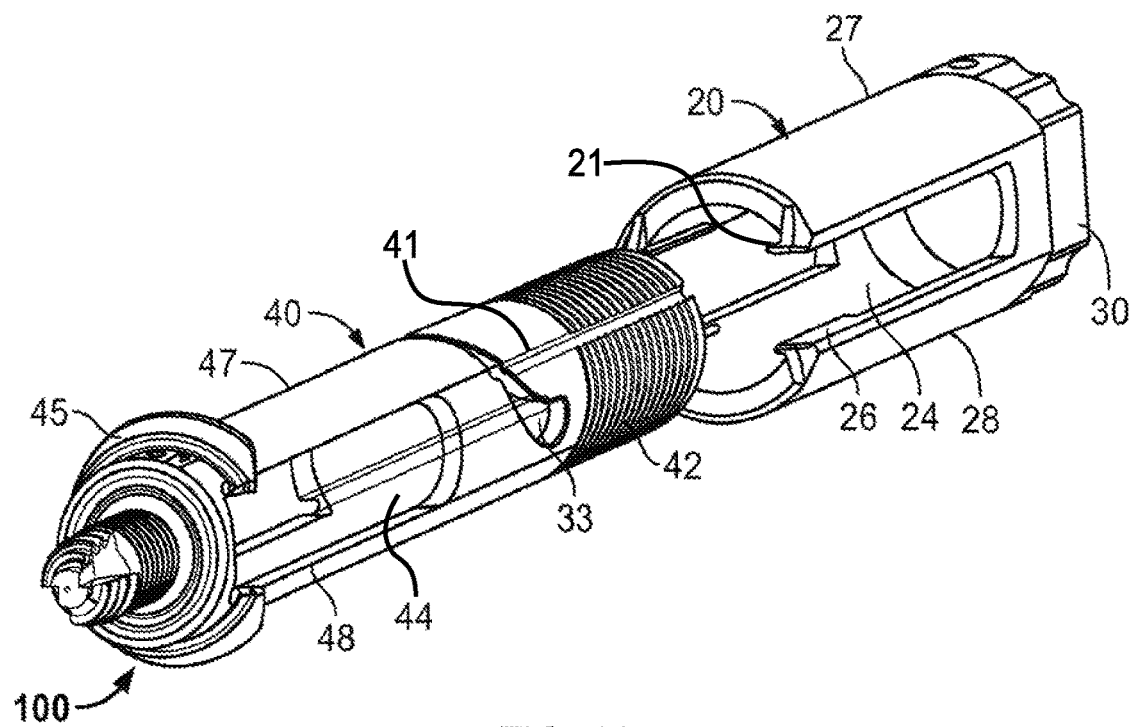
FIG. 1A is a more extreme perspective end view showing the inner shaft and rod receiving implant coupled and the outer shaft separated.

With reference to FIG. 1, a screw extension assembly 10 is illustrated. The screw extension assembly 10 has an outer shaft 20 and an inner shaft 40. As shown, at a distal end of the screw extension assembly 10 is a rod receiving implant 100. The rod receiving implant 100 has a rod holding element 101 and a bone or pedicle screw 120 extending from the base of the rod holding element 101. The rod holding element 101 is slotted and configured to receive a spinal rod. As shown in FIGS. 1 and 1A, the inner shaft 40 has slots 44 defining deflectable leg extensions 47, 48. The deflectable leg extensions 47, 48 have a distal end 45 configured to deflect and engage the rod holding element 101. The rod holding element 101 has a groove 109 configured to engage a projection 49 on the distal end 45 of the deflectable legs 47, 48, best shown in FIG. 3A.

With further reference to FIG. 1A, the outer shaft 20 has a proximal end with a rotatable locking knob 30 affixed thereto. The outer shaft 20 has a slotted opening 24 on each side defining legs 27, 28 on the outer shaft 20. The leading edge of the outer shaft 20 has a chamfered end 26. The chamfered end 26 along edges of the slotted openings 24 has rails 21 that project and extend along the length of the outer shaft 20. These rails 21 are configured to fit in grooves 41 that run longitudinally relative the inner shaft 40. The inner shaft 40 additionally has threads 42 at a proximal end and a groove 33 configured to receive a pin 32 as shown in FIG. 2 on the rotatable locking knob 30.

Figure 2:
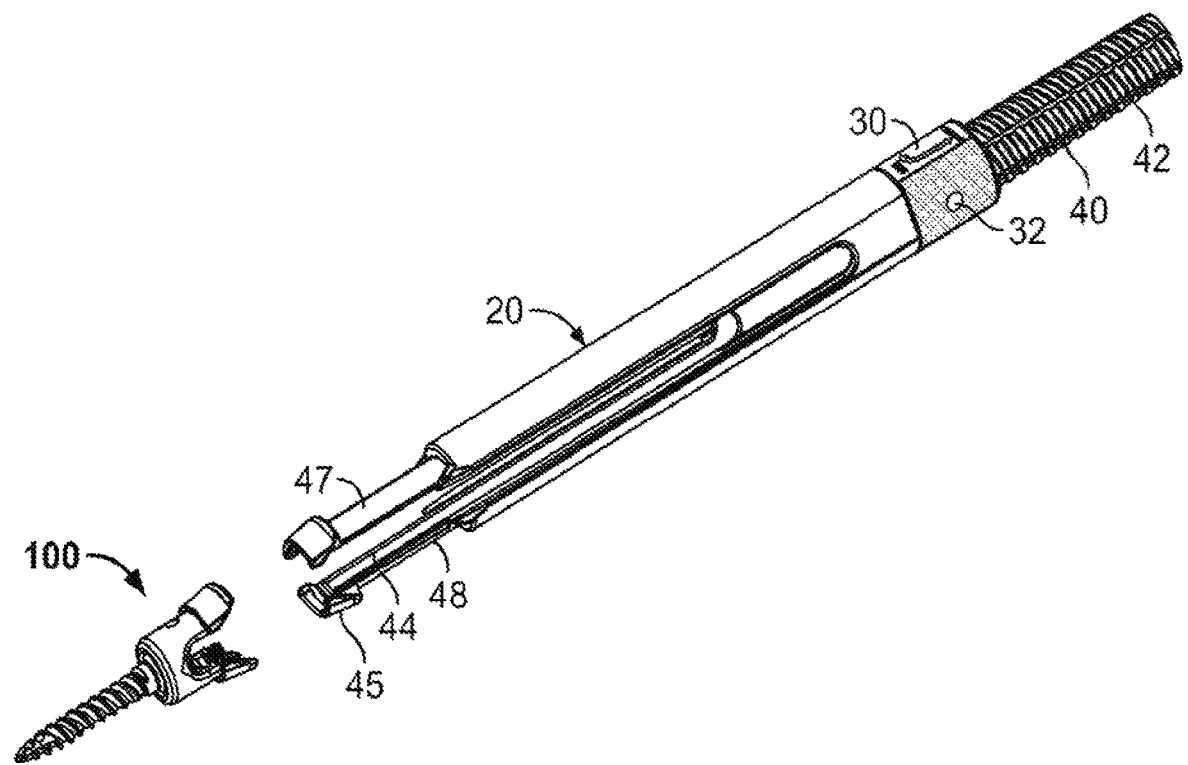
FIG. 2 is a side perspective view taken from FIG. 1.
Figure 2A:
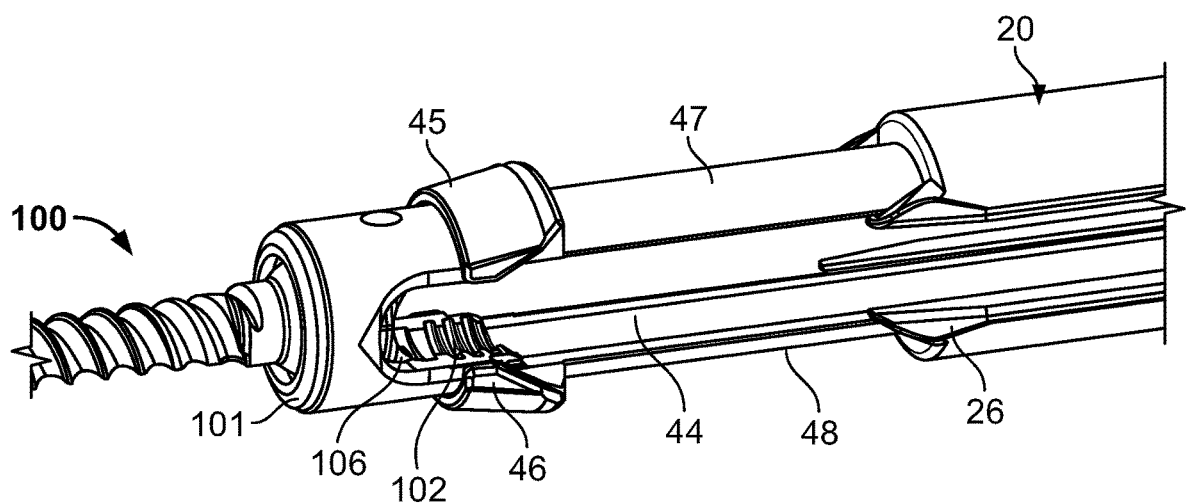
FIG. 2A is an enlarged view of the distal end of the inner shaft taken from FIG. 2.
Figure 2B:
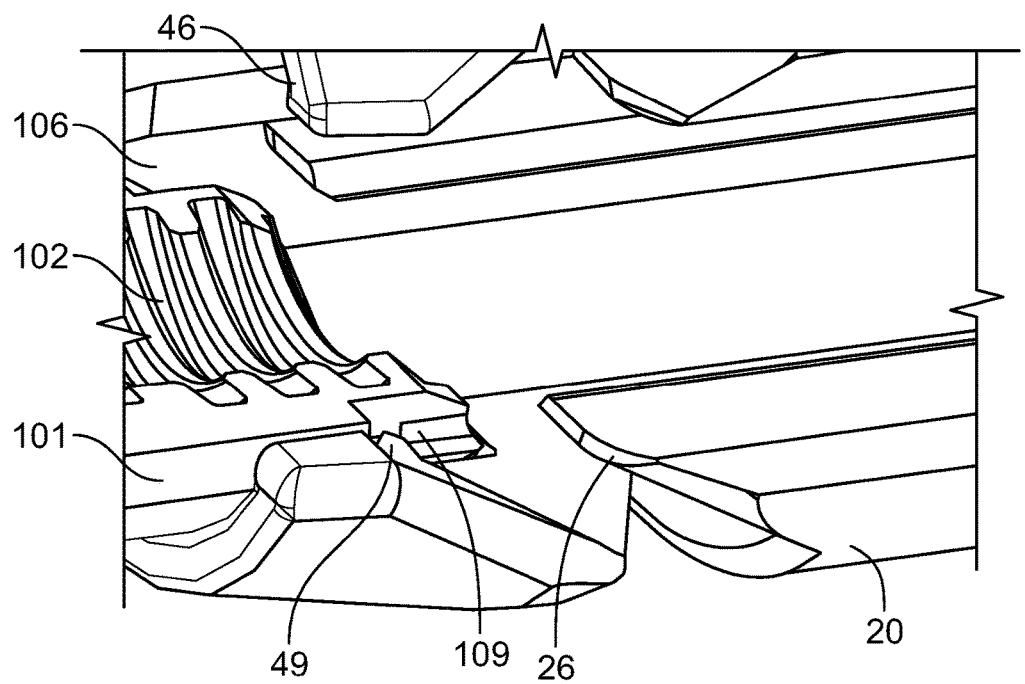
FIG. 2B is a further increased enlarged view of the inner shaft coupled to the rod holding element as the outer shaft translates distally.

As shown in FIG. 2, when the outer shaft 20 is slid over the inner shaft 40, the rails 21 engage the grooves 41 so that the two are coupled together in such a fashion that they are non-rotatable relative to the other. As shown in FIG. 2, as the distal end of the outer shaft 20 slides toward the distal end 45 of the inner shaft 40 the slots 44 and 24 start to overlap. With reference to FIG. 2A, the rod holding element 101 has internal threads 102. The deflectable legs 47, 48 at the distal end 45 are shown engaged with the rod holding element 101. The outer shaft 20 with its chamfered end 26 is shown proximally spaced from the distal end 45 in FIG. 2A. As the outer shaft 20 is moved forward, as shown in FIG. 2B, the chamfered end 26 starts to engage the distal end 45 of the inner shaft 40. As shown, the rod holding element 101 has a groove 109, shown in FIG. 2B, in which the distal end 45 has a projection 49 that engages this groove 109 clipping the deflectable legs 47, 48 onto the rod holding element 101. The rod holding element 101 further has a cutaway section 106 which is encircled by the end 46 such that the projection 49 is locked between a portion of the rod holding element 101 on an outer surface and extends outwardly to where it is exposed as shown in FIG. 2B.

Figure 2C:
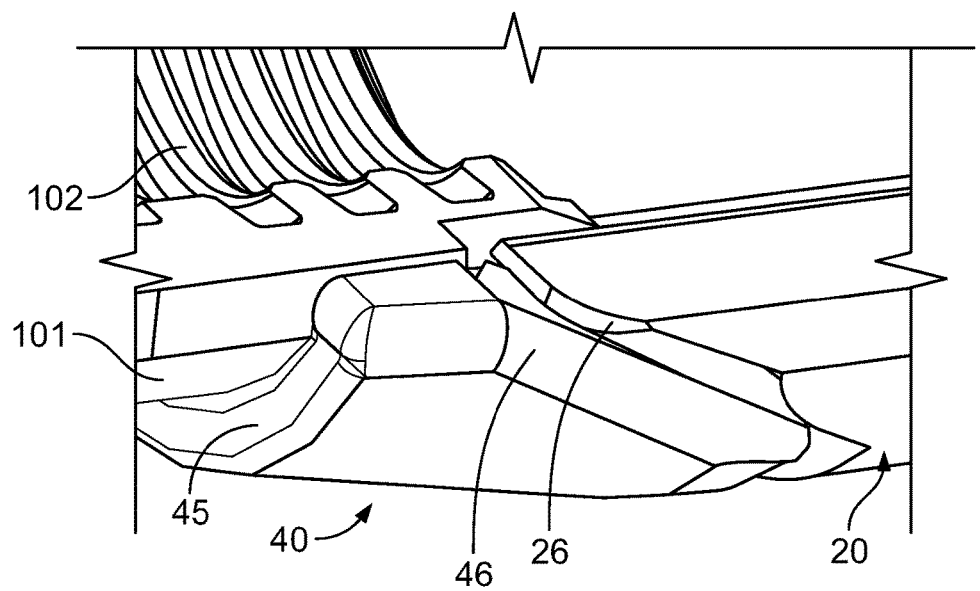
FIG. 2C is the view taken from FIG. 2B showing the outer shaft engaging internal portions of the rod holding element just prior to being fully engaged and locked.

As shown in FIG. 2C, as the outer shaft 20 moves further inwardly into an engaged position. The chamfered end 26 covers that portion of the rod holding element 101 along an inner surface of the slot defining the rod holding element 101. When this occurs, the rod holding element 101 is held externally by the deflectable legs 47, 48 and internally by the end 46 and also locked from rotation movement as the chamfered end 26 engages edges of the rod holding element 101.

Figure 3:
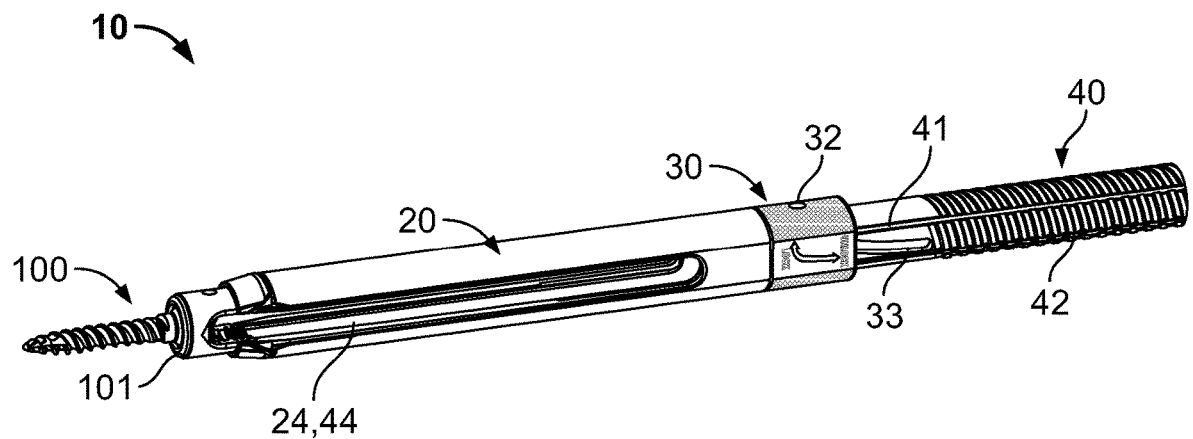
FIG. 3 is a side perspective view showing the outer shaft in a fully engaged and locked position.
Figure 3A:
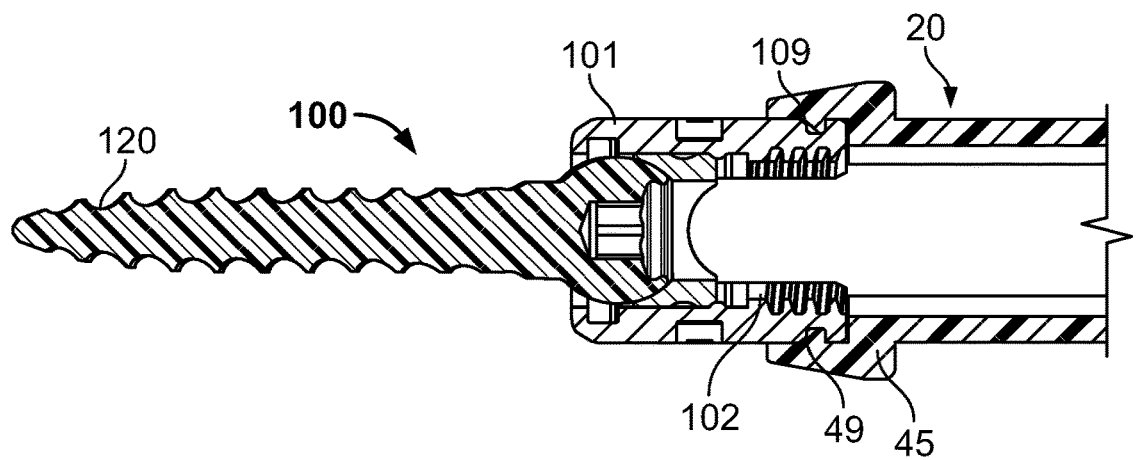
FIG. 3A shows a partial cross-section of the rod holding element locked and held by the inner shaft.

With reference to FIG. 3, the screw extension assembly 10 is shown in the fully engaged and locked position. To better appreciate how this occurs, a cross-sectional view, FIG. 3A, is illustrated showing the rod receiving spinal implant 100 and rod holding element 101 fully locked into the distal end of the deflectable legs 47, 48 and locked rigidly into place by the outer shaft 20.

Figure 3B:
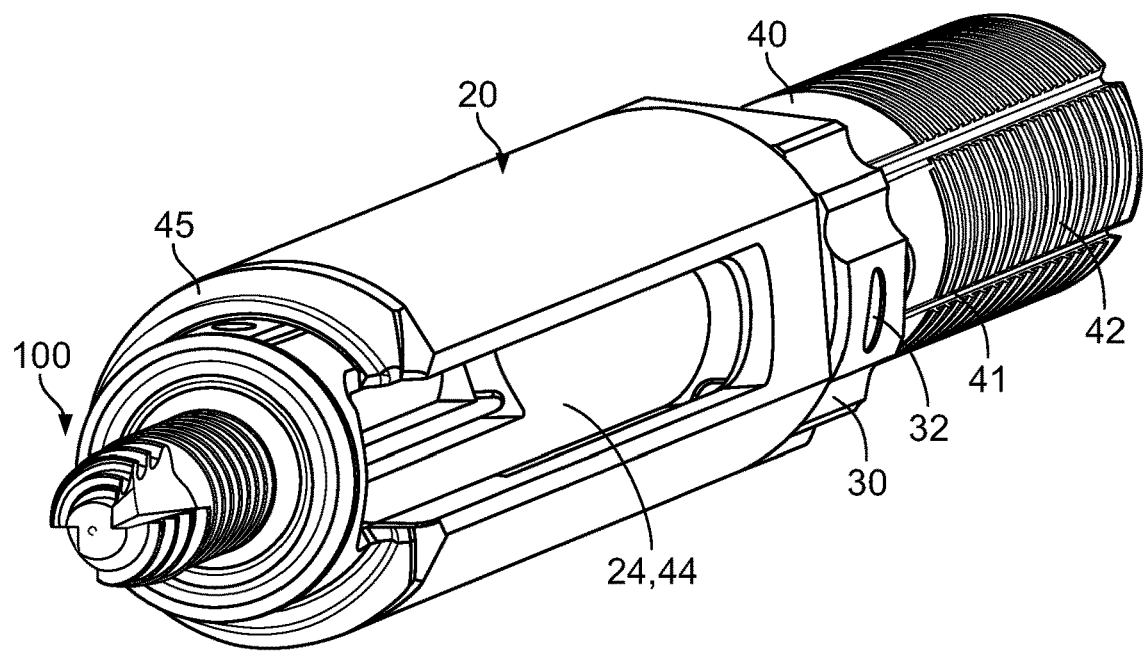
FIG. 3B shows the locking knob prior to being moved to a locked position.

With reference to FIG. 3B, when the outer shaft 20 and inner shaft 40 are engaged with the spinal implant 100, the knob 30 is positioned 90 degrees off its final locked position. A counter clockwise 90 degree rotation of the knob 30 will cause the assembly to lock into a locked position from this engaged position shown in FIG. 3B.

Figure 3C:
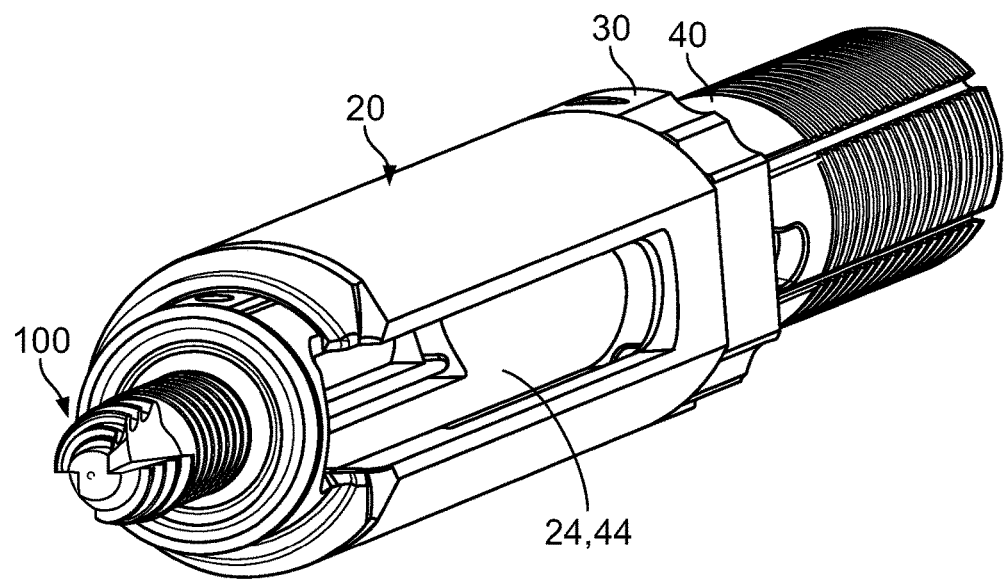
FIG. 3C shows the locking knob rotated 90 degrees toward a locked position.

FIG. 3C shows this rotation. When this rotation is accomplished, the spinal implant 100 is fully locked onto the screw extension assembly 10.

Figure 3D:
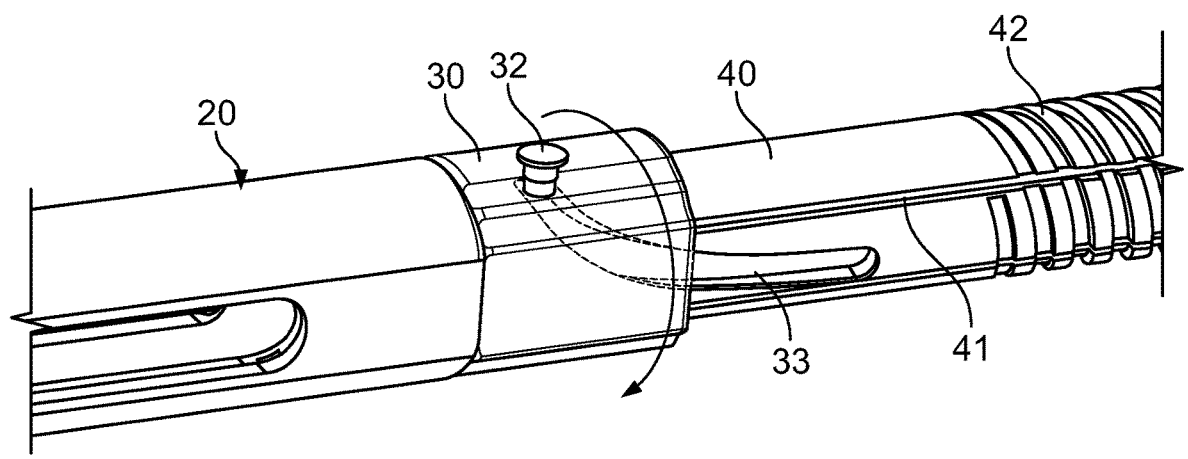
FIG. 3D shows a side view of the locking knob fully moved to the locked position.

With reference to FIG. 3D, the fully engaged position is shown. When this occurs, the locking knob 30 has moved upwardly through a cam groove 33 guided by one or more pins 32.

Figure 4A:
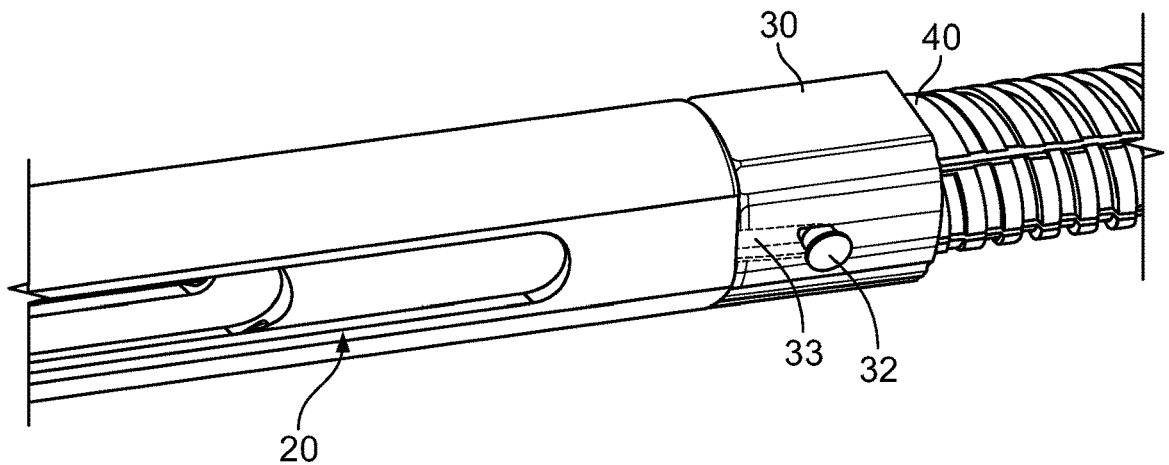
FIGS. 4A, 4B and 4C show the locking knob in phantom with a fixed pin in the one or more cam grooves, wherein the pin is shown moving in the cam groove in FIG. 4B as the knob is rotated to the engaged position of FIG. 4C to the fully locked position of FIG. 4D.
Figure 4B:
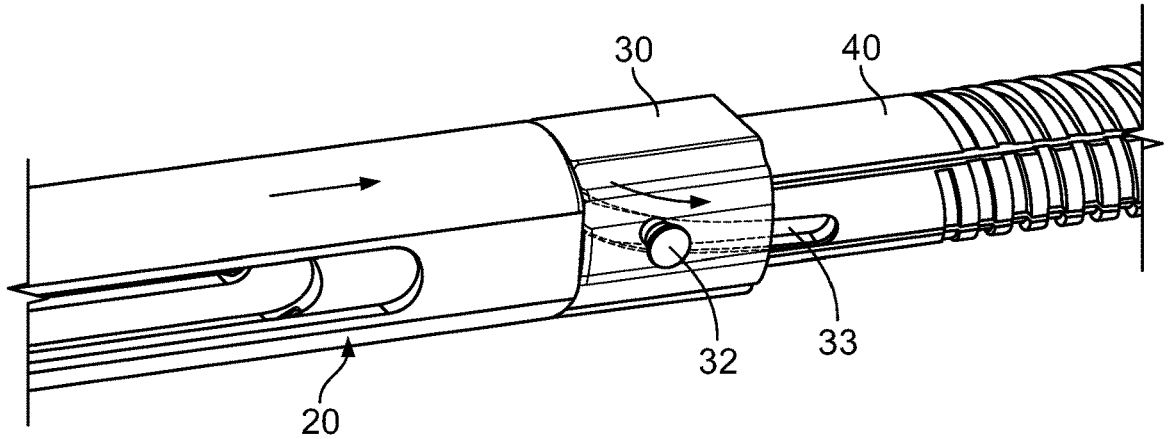
Figure 4C:
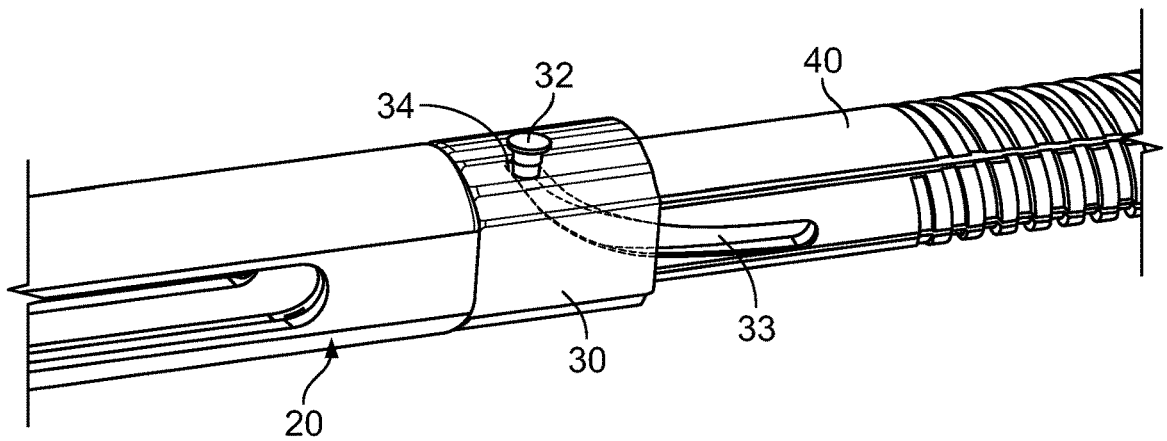

This rotation and movement is best seen in FIGS. 4A-4C. In FIG. 4A, the pin 32 is shown in an aft position with the locking knob 30 illustrated in phantom. As the knob 30 is being moved toward the distal end as it is being rotated counter clockwise, FIG. 4B shows the pin 32 following the groove 33. Once the groove 33 has moved from the positon in 4B, the pin 32 hits a section 34 of the groove 33 defined as a cam over projection 34 shown in FIG. 4C. When this occurs, there is a noticeable locking of the knob 30 so it cannot be moved unless physically moved out of the cam over position.

Figure 5:
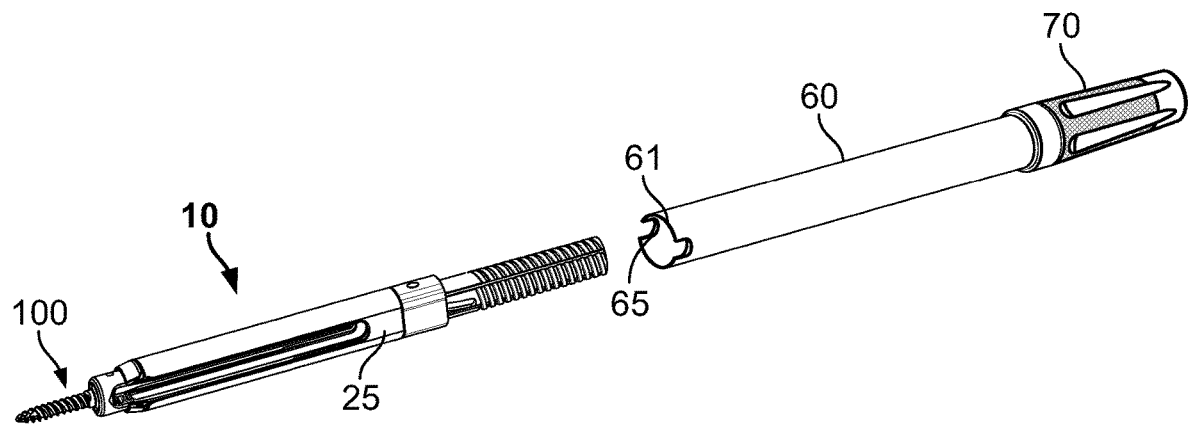
FIG. 5 is an exploded view of the inner and outer shafts assembled and coupled to a rod receiving implant with a rod reducer tube being aligned to pass onto the assembly.
Figure 6:
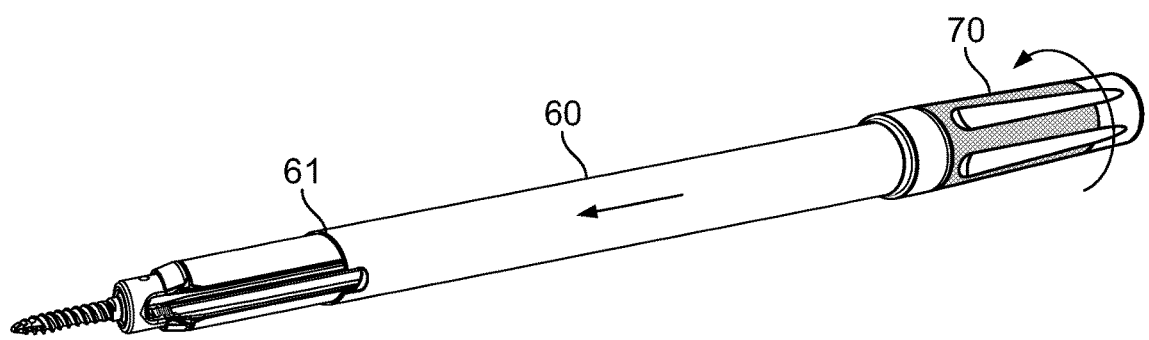
FIG. 6 shows the rod reducer onto the assembly.
Figure 7:
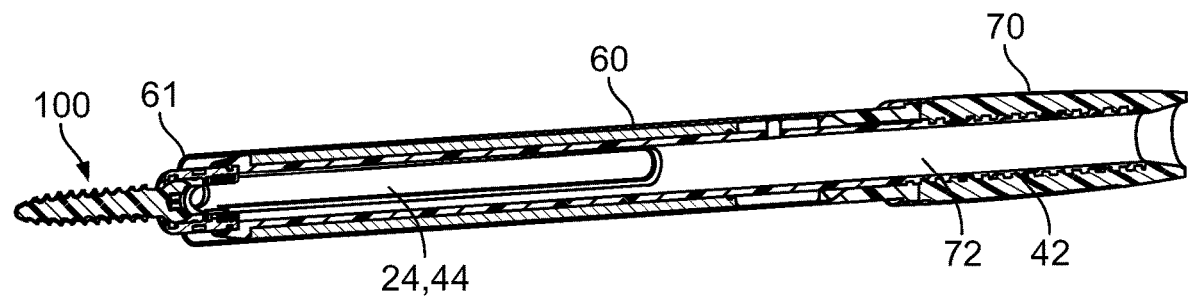
FIG. 7 shows the rod reducer tube being pushed distally toward a rod seated position by the rotation of the abutting removable nut.

Once the screw extension assembly 10 is fitted over the rod holding element 101, a reducer tube 60 can be positioned over the assembly 10, as shown in FIGS. 5 and 6. A separate nut 70 can be provided. The nut 70 abuts the proximal end of the tube 60. The nut 70 can alternatively be captively held to the reducer tube 60, but free to rotate relative to the reducer tube, if so desired. The tube 60 has a distal end 61 which has a cavity for engaging a spinal fixation rod and to reduce that rod when the reducer tube 60 is positioned over the assembly 10 as shown in FIG. 6. When this occurs, end 61 is positioned upwards of the slots 24, 44 which are coaligned. As the reducer 60 is moved forward by rotation of the nut 70, the reducer tube 60 translates forward. As shown, the reducer tube 60 has flats 65 that align with the external flats 25 on the outer shaft 20. These coaligned flats prevent the reducer tube 60 from rotating about the assembly and guide the reducer tube 60 down the shaft 20 as the nut 70 translates. Interestingly, the nut 70 is shown as a separate component, so that it can easily be removed leaving the reducer tube 60 in position, if so desired. The nut 70 has internal threads 72 that engage threads 42 of the inner shaft 40.

Figure 8:
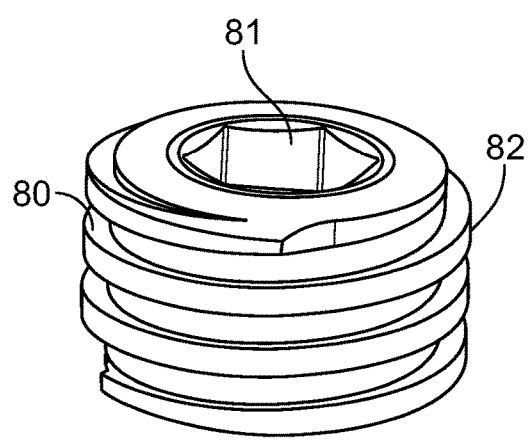
FIG. 8 is a perspective view of an exemplary set screw for fixing a rod.

With reference to FIG. 8, an exemplary set screw 80 is shown. The set screw has a driving recess 81 and external threads 82. The external threads 82 are configured to engage internal threads 102 of the rod holding element 101.

Figure 9:
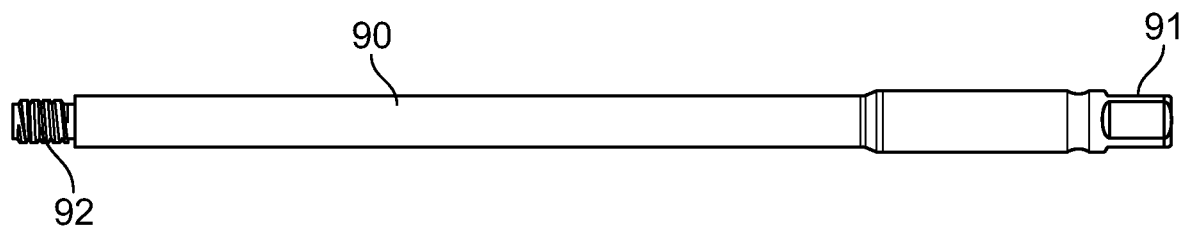
FIG. 9 is a view of an exemplary set screw driver.

With reference to FIG. 9, an exemplary set screw driver 90 is shown with the handle removed. The set screw driver 90, as shown, has a threaded end 92 for receiving a handle and a driving end 91 for engaging a set screw.

Figure 10:
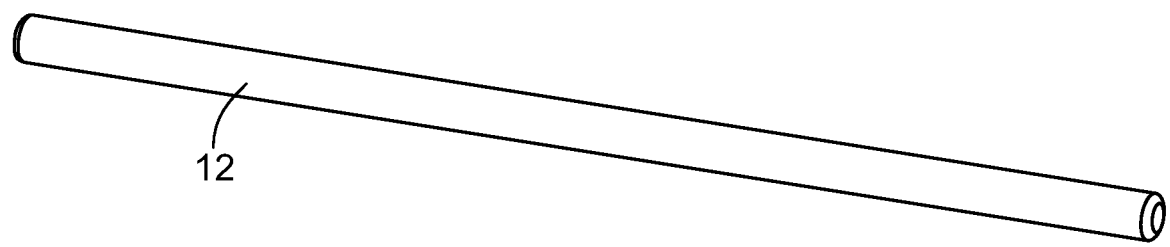
FIG. 10 is s view of an exemplary fixation rod.

With reference to FIG. 10, an exemplary spinal fixation rod 12 is illustrated with a cylindrical, solid body designed for spinal fixation.

Figure 11:
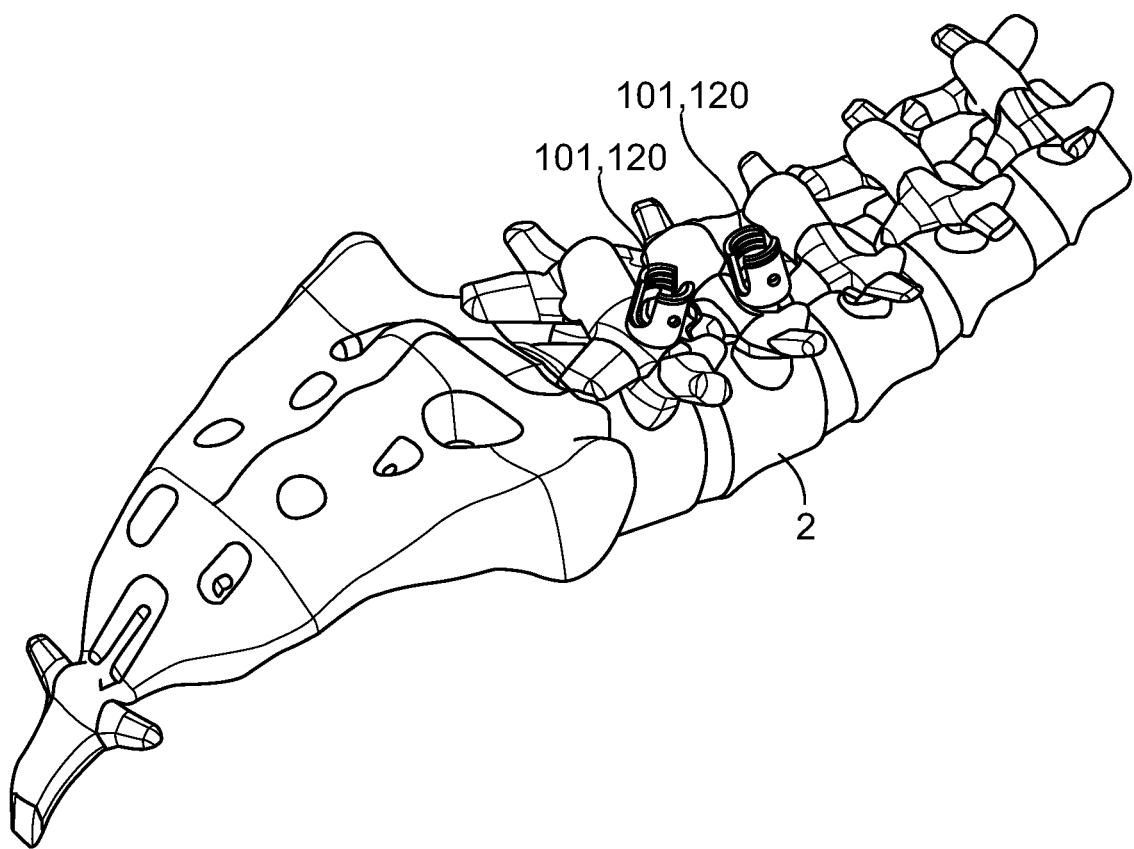
FIG. 11 is a perspective view of an exemplary spine with two of the rod holding elements and bone screws prepositioned to have a fixation rod installed.

With reference to FIG. 11, a perspective view of a portion of a spine 2 is illustrated. The spine 2, as shown, has a rod holding element 101 with a bone screw 120 embedded into a vertebrae. A pair of these assemblies are shown in adjacent vertebrae and are prepositioned to receive a spinal fixation rod.

With reference to FIGS. 12A-12M, the fixation of the spinal rod using the screw extension assembly 10 for use in minimally invasive spinal surgery is illustrated showing a step by step procedure of using this assembly 10 of the present invention.

Figure 12A:
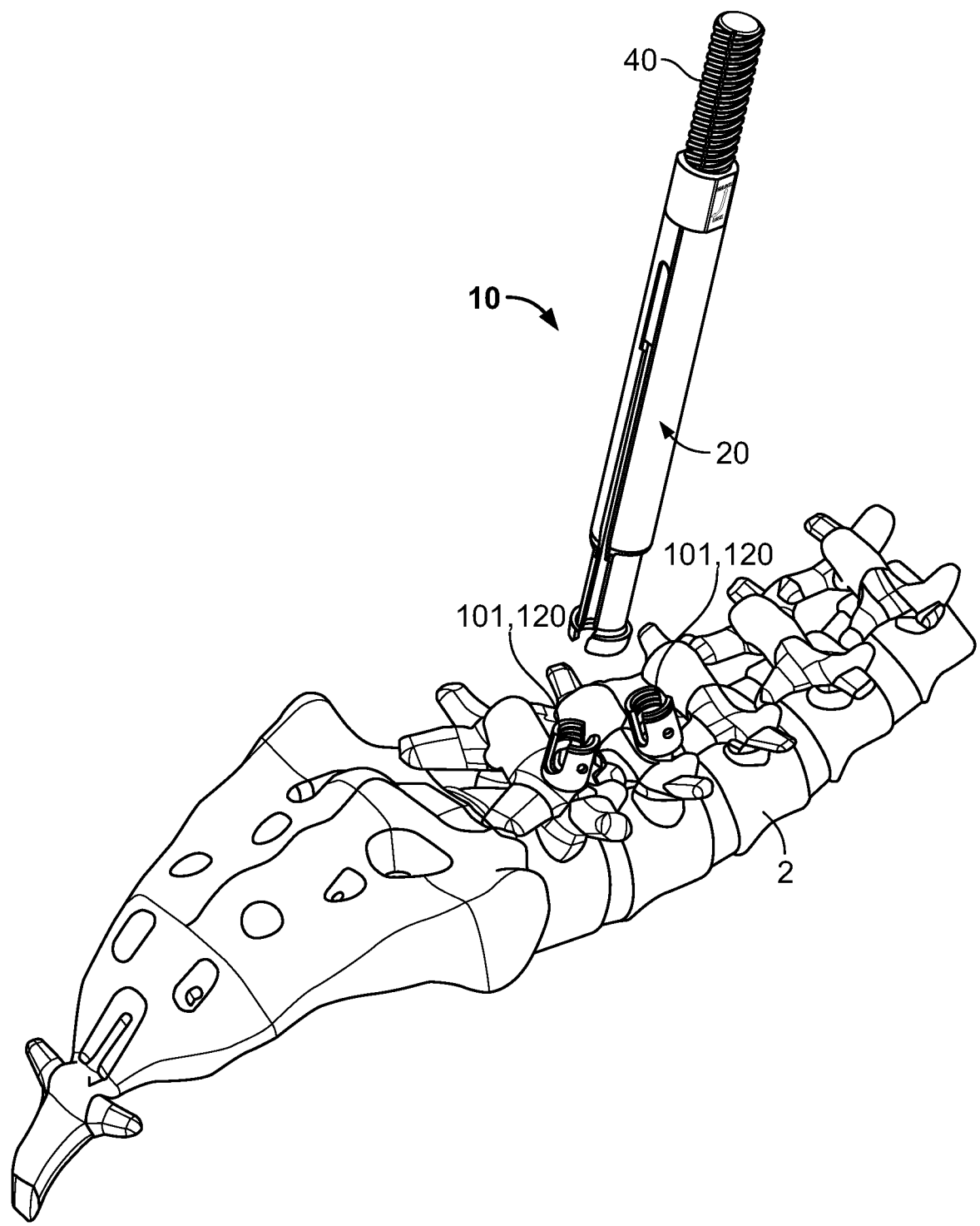
FIGS. 12A-12M are views of the screw extension assembly and reducer being used to seat and fix a spinal fixation rod into the pair of prepositioned slotted rod receiving implants shown in FIG. 11.
Figure 12B:
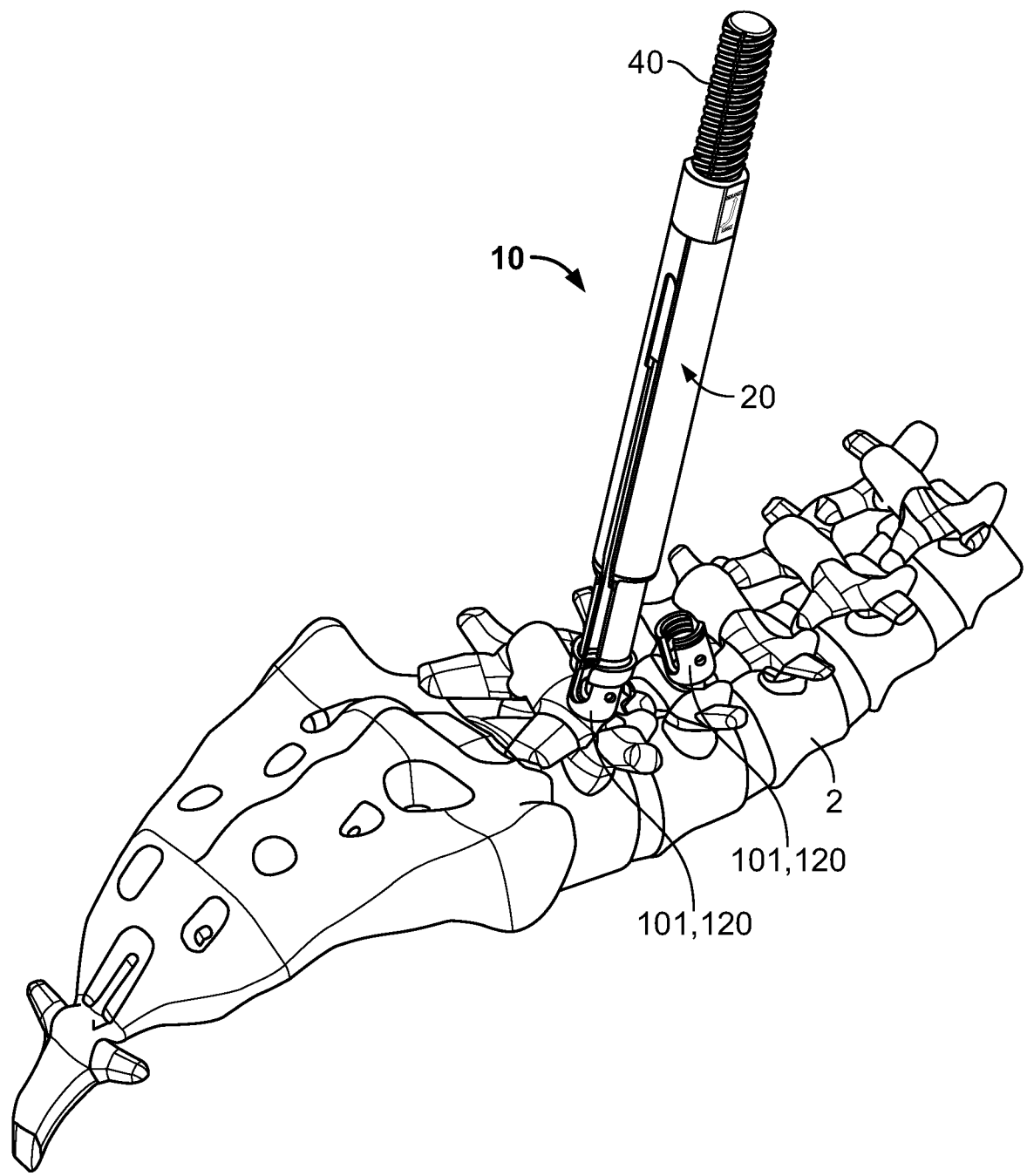
Figure 12C:
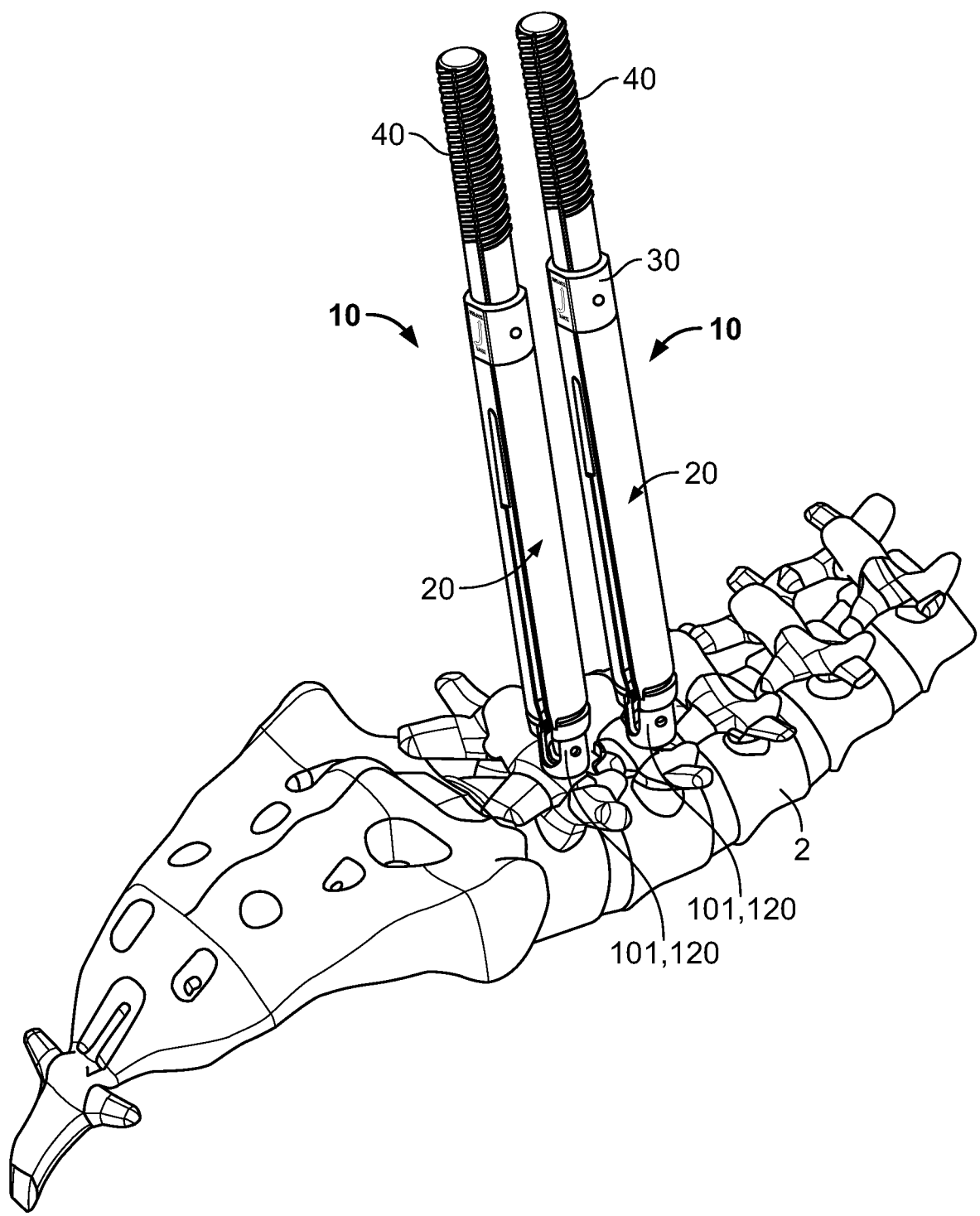
Figure 12D:
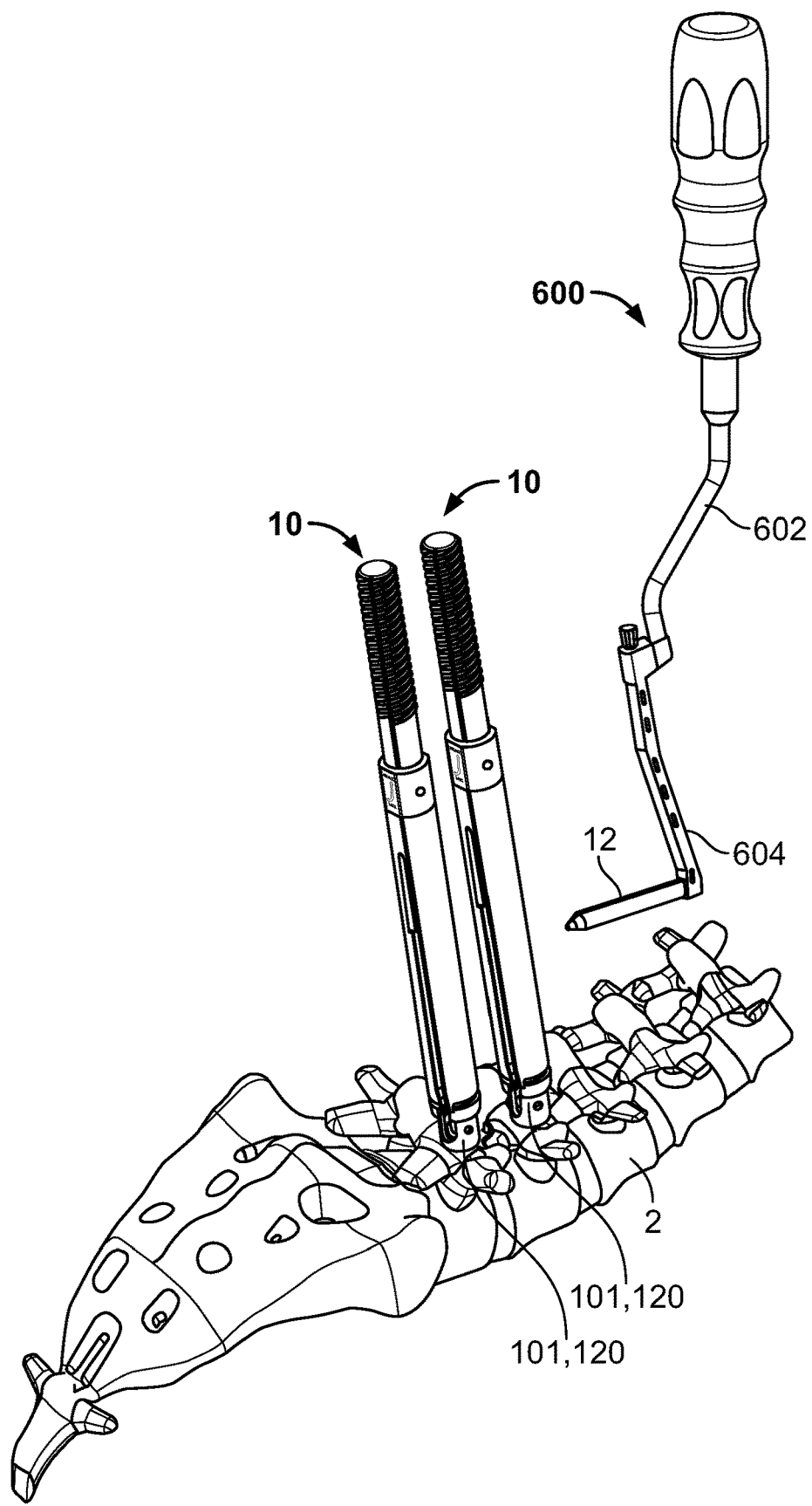
Figure 12E:
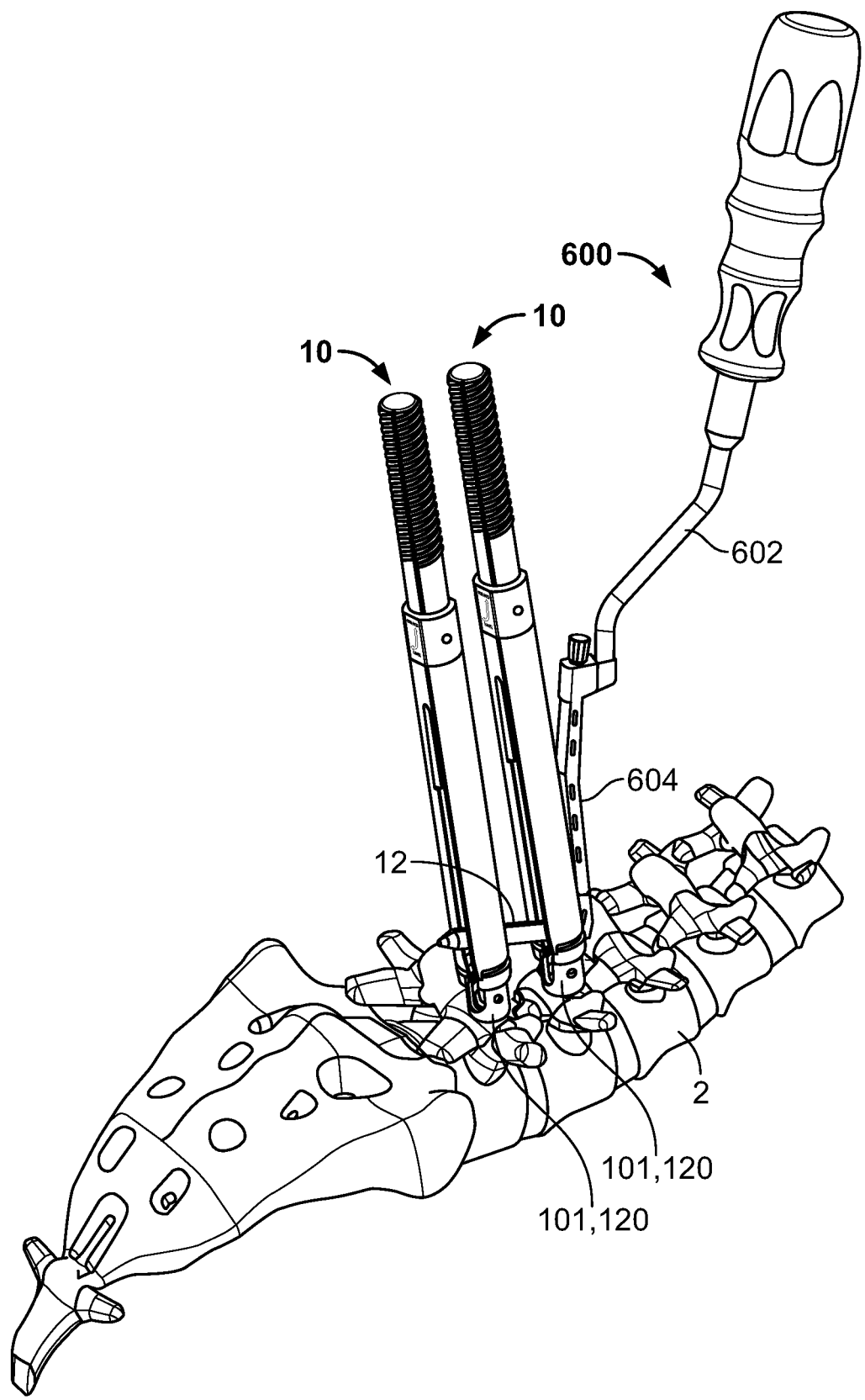
Figure 12F:
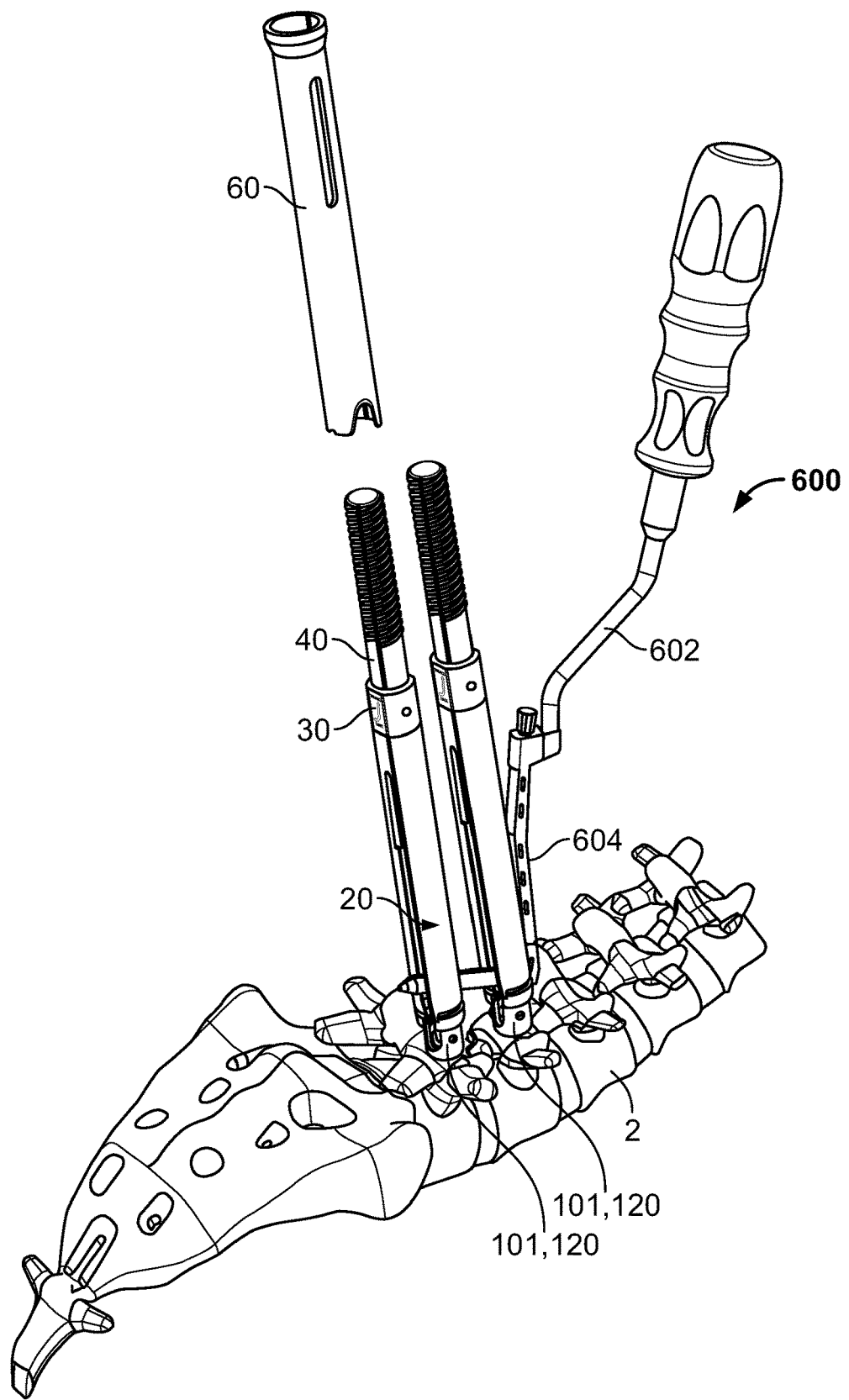
Figure 12G:
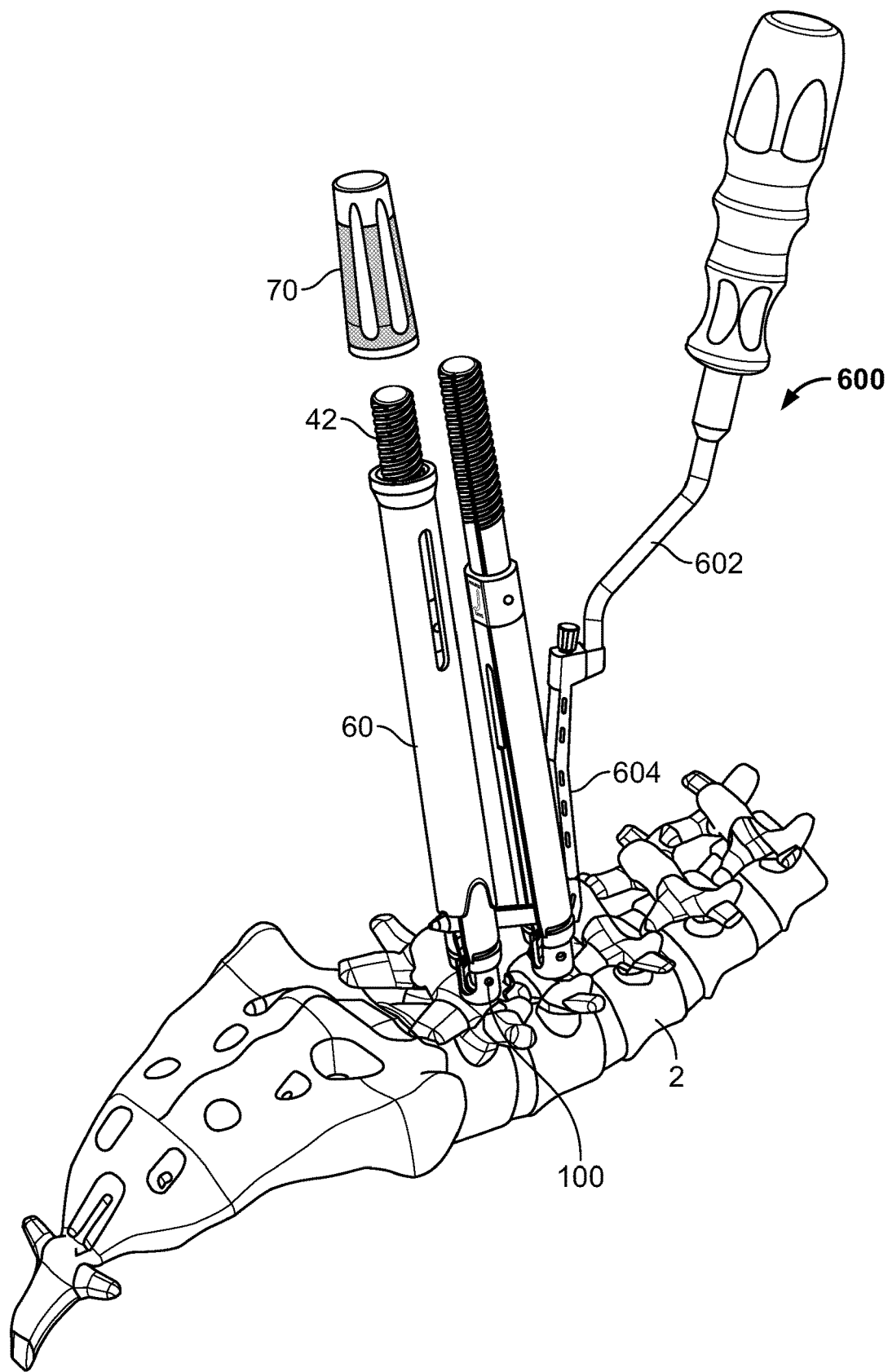
Figure 12H:
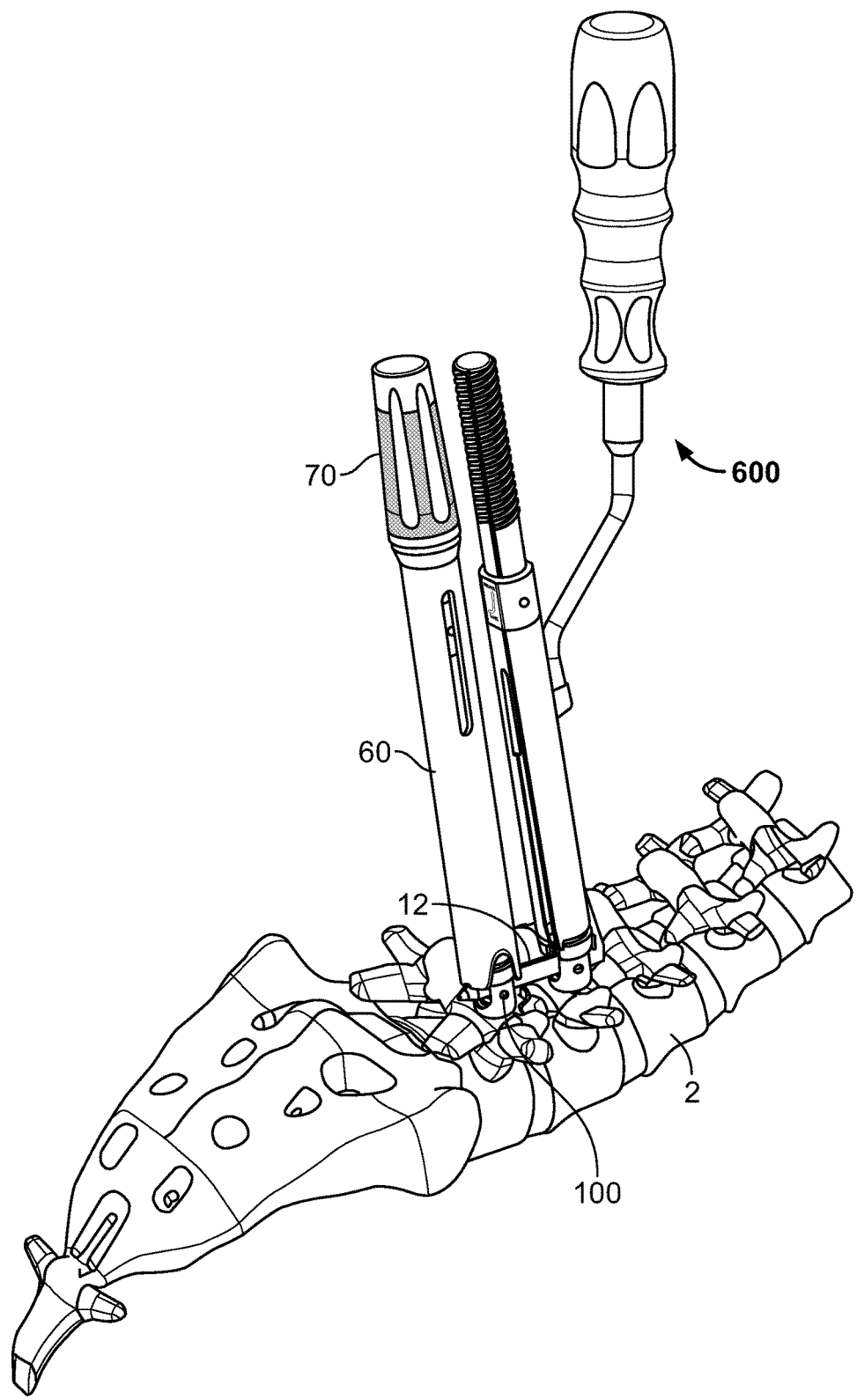
Figure 12I:
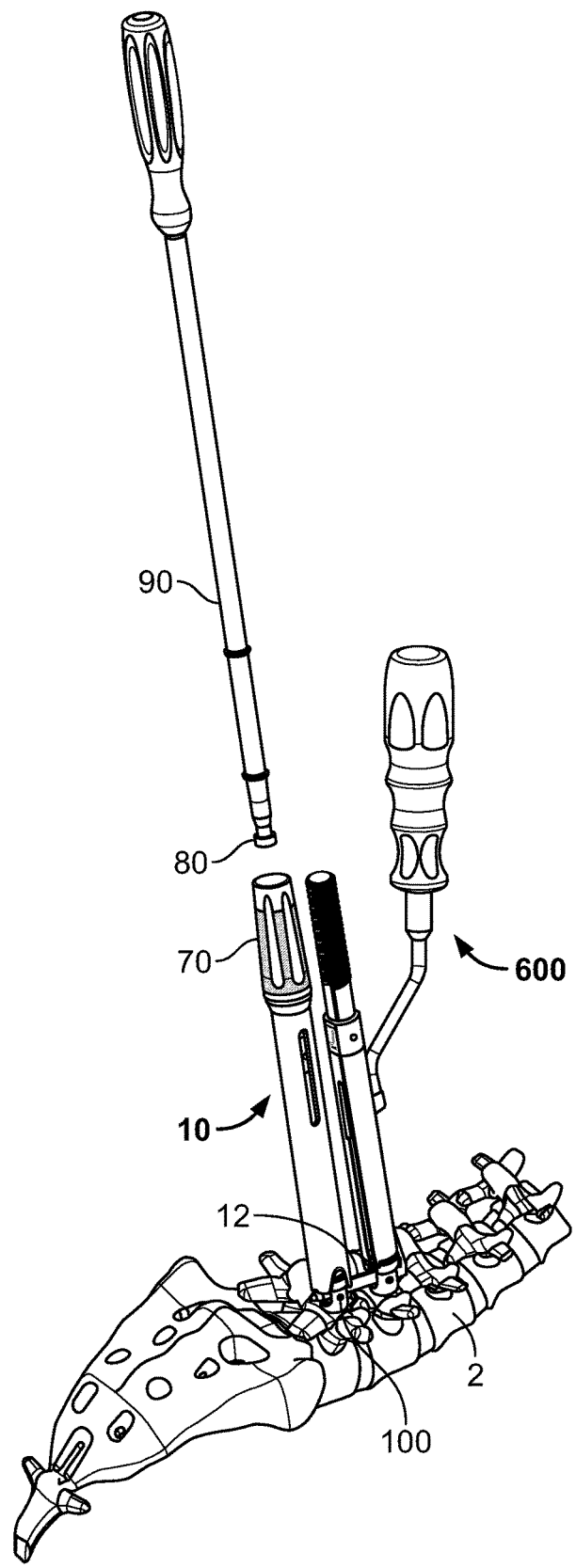
Figure 12J:
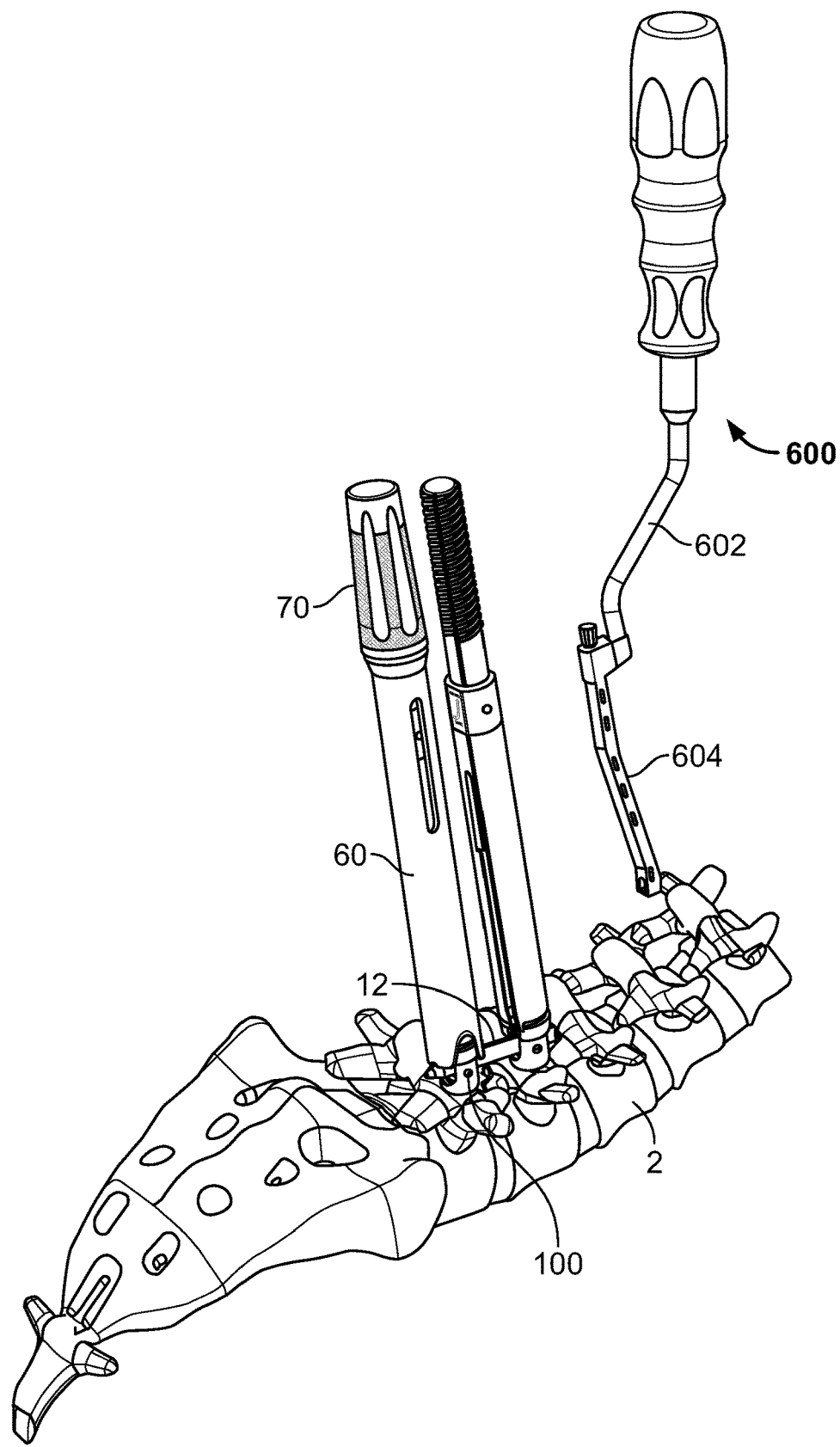
Figure 12K:
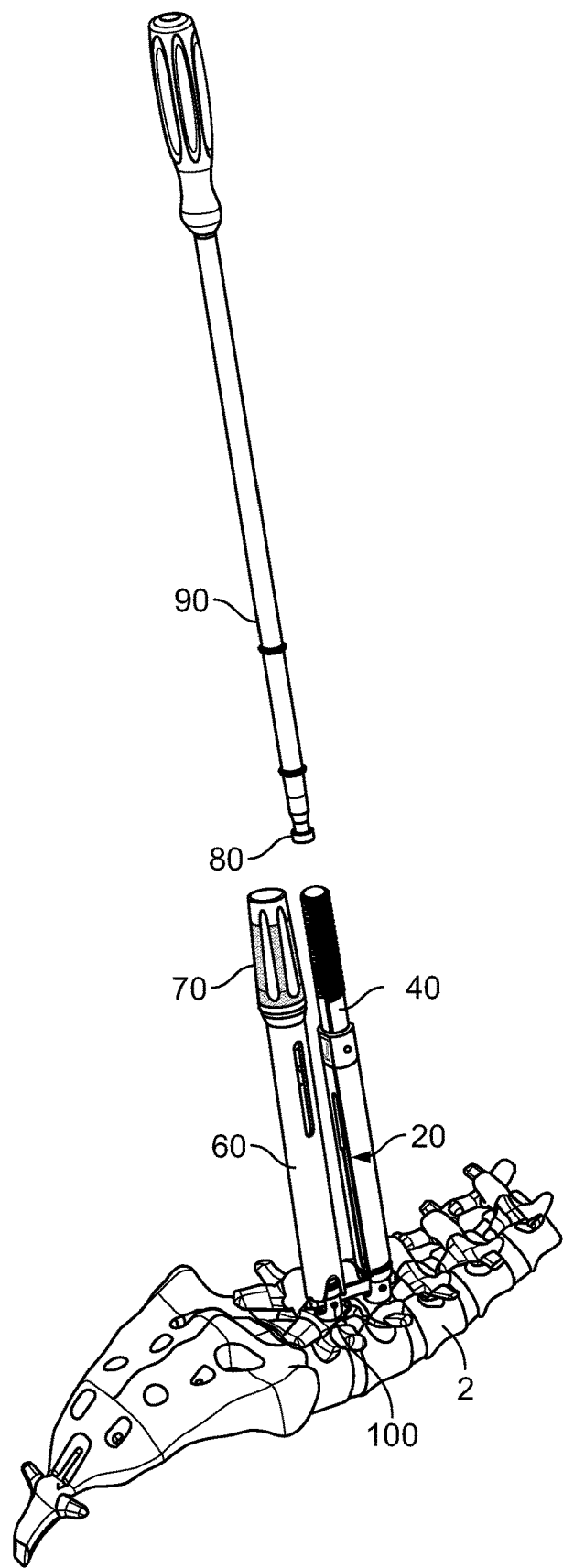
Figure 12L:
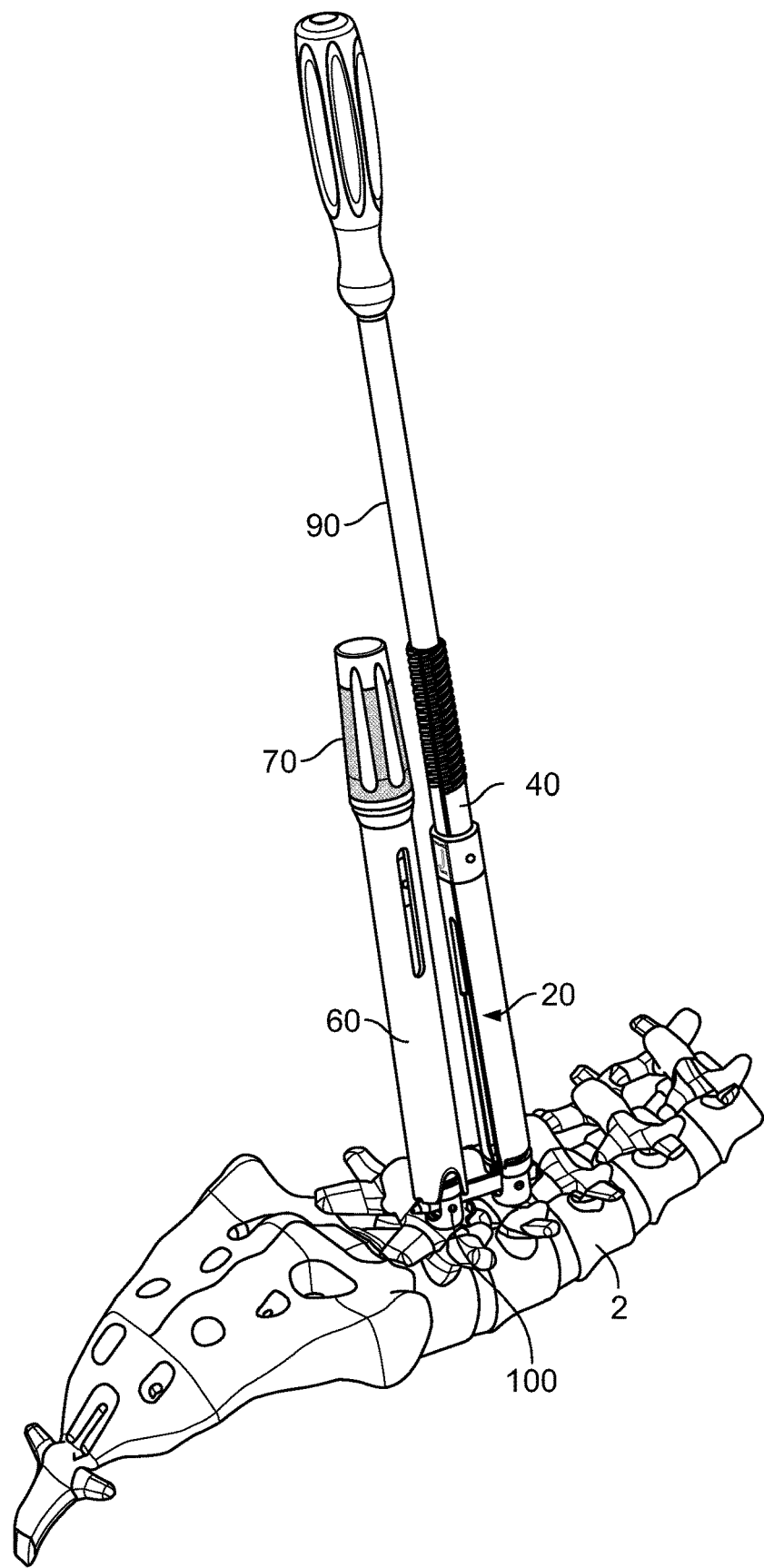
Figure 12M:
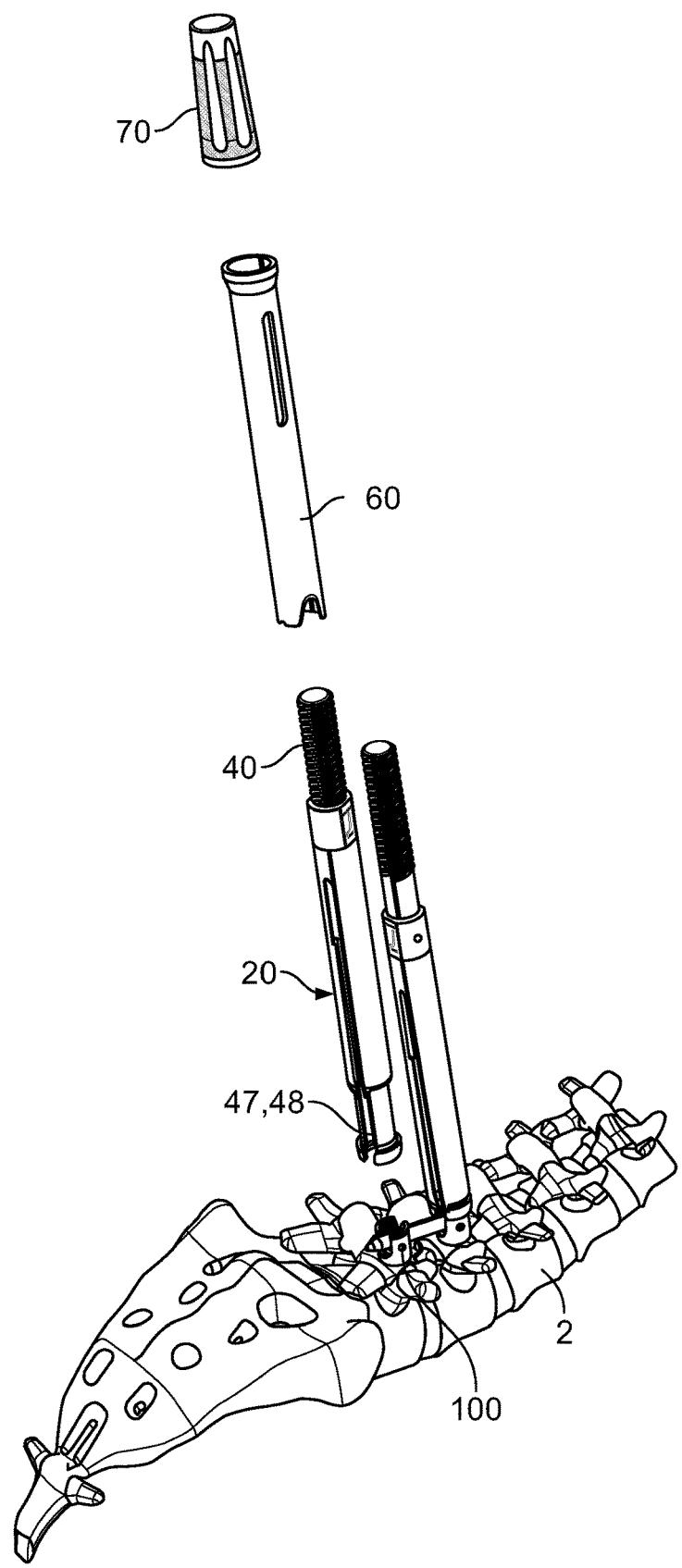

With reference to FIG. 12A, the assembly 10 with the inner shaft 40 and outer shaft 20 is prepositioned to align with one of the rod holding elements 101. With reference to FIG. 12B, the assembly 10 is shown with the deflectable leg extensions 47, 48 positioned onto the groove 109 of the rod holding element 101. To accomplish this, the surgeon just pushes down on the assembly 10 and the legs 47, 48 automatically deflect outwardly and the projections 49 will then engage the rod holding element groove or recess 109. With reference to FIG. 12C, two of the screw extension assemblies 10 are shown, one prepositioned on each of the rod holding elements 101. As shown in FIG. 12C, the outer shaft has been moved directly inwardly covered thereby encircling the distal end 45 of the leg extensions and the locking knob 30 has been rotated into the fully engaged position, as illustrated. With reference to FIG. 12D, a rod delivery tool 600 is shown. The rod delivery tool 600 has an arm 602 and a shaft 604 adapted to receive and hold an end of a spinal fixation rod 12. As shown, the fixation rod 12 is being aligned in FIG. 12D such that the slotted openings 24, 44 of the inner and outer shafts of each assembly 10 are aligned so as to receive the fixation rod 12. With reference to FIG. 12E, the surgeon will now have moved the rod delivery tool 600 in such a fashion that the fixation rod 12 is now positioned in the slotted openings 24, 44 of each assembly 10. In this position, the rod 12 is positioned to be seated. With reference to FIG. 12F, the reducer tube 60 can now be positioned over one of the assemblies 10 and the rod delivery tool 600 is still shown holding the rod 12 in position at this point. Once the reducer tube 60 is positioned over the assembly 10, a removable nut 70 as shown in FIG. 12G is positioned above the threads 42 of the inner shaft 40. The removable nut 70, when tightened, as shown in FIG. 12H, drives the reducer tube 60 distally pushing against the fixation rod 12. When the nut 70 is fully turned and the fixation rod 12 is fully seated in the rod receiving implant 100, then as shown in FIG. 12I, a set screw 80 shown attached to a set screw driver 90 can be passed through the nut 70 and the assembly 10 inwardly towards the distal end to engage the internal threads 102 of the rod holding element 101, as shown in FIG. 12I. Once this is accomplished, the set screw 80 is securely holding the fixation rod 12 in position, as shown in FIG. 12J. When this occurs, as shown in FIGS. 12K and 12L, a second set screw 80 can be attached to the driver 90 and it can be delivered to the second assembly 10 to fix the opposite end of the fixation rod 12 into the second rod receiving implant 100. It is noted that the reducer tube 60 has not been used on the second rod holding element 101 because it is believed that seating the rod 12 in the first rod holding element 101 will deliver and hold the rod 12 tightly and securely in position sufficiently low that the set screw 80 can engage the threads 102 of the second rod holding element 101. If however, it is determined that the rod 12 needs to be reduced on the second rod receiving implant 100, the reducer tube 60 and nut 70 can be employed as previously discussed in 12F-12H. This however, should not be necessary when the rod 12 is securely positioned in one of the rod receiving implants 100 as it should have lowered the entire rod 100 into seated positions in both implants 100. Once the set screw 80 is delivered to the second assembly 10 and tightened and engaged to the internal threads 102 of the rod holding element 101, the set screw driver 90 can be removed. Once the set screw driver 90 has been removed, similarly the nut 70 can be removed from the threaded portion of the inner shaft 40 and the reducer tube 60 can be removed. When the reducer tube 60 is removed, the locking knob 30 can be rotated and the outer shaft 20 can be pulled back distally, this releases the deflectable legs 47, 48 of the inner shaft 40 from the locked position and at this point with the outer shaft 20 pulled proximally away from the distal end 45, the deflectable legs 47, 48 can be simply deflected off of the fixed rod 12 and spinal rod receiving implant 100, as shown in FIG. 12M. Finally, not illustrated, the second assembly 10 can be similarly removed simply by turning the locking knob 30 into the unlocked position and proximally moving the outer shaft 20 to disengage from the locking positon so the deflectable legs 47, 48 of the inner shaft 40 of the second assembly 10 can be freely deflected to disengage the second spinal rod receiving implant 100. Once this is accomplished, the assembly of the fixation rod 12 will be complete between the two spinal rod receiving implants 100.

Variations in the present invention are possible in light of the description of it as provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A kit for use in minimally invasive spinal surgery, the kit comprising:
    a rod receiving implant, the rod receiving implant having a rod holding element and a threaded bone fastener extending distally from the rod holding element;
    an inner shaft comprising an elongated hollow tubular shaft having a proximal end with a threaded portion, a distal end, and a slotted distal end portion having a pair of inner shaft slots open through the distal end defining a pair of deflectable leg extensions, each leg extension comprising a projection configured to engage grooves on the rod holding element thereby coupling the inner shaft to the rod holding element at the distal end of each leg extension;
    an outer shaft configured to translate about the inner shaft, wherein the outer shaft comprises a pair of outer shaft slots open through an outer shaft distal end with longitudinal rails adjacent edges of each of the outer shaft slots to slide along each edge of the inner shaft slots, wherein the threaded portion of the inner shaft has longitudinally extending grooves aligned to receive the longitudinal rails of the outer shaft;
    wherein the outer shaft, when translated toward the distal end of the inner shaft and into an engaged position, locks the deflectable leg extensions in a coupled position to the grooves of the rod holding element, wherein the pair of deflectable leg extensions abut an outer surface of the rod holding element and the outer shaft distal end engages an internal surface of the rod holding element;
    a rod reducer, wherein the outer shaft and the rod reducer have complementary flats extending longitudinally to allow the rod reducer to translate, but not rotate, relative to the outer shaft; and
    a nut for engaging the threaded portion of the proximal end of the inner shaft, wherein the nut abuts a proximal end of the rod reducer to translate the rod reducer upon tightening to move a rod into a seated position in the rod holding element.

2. The kit of claim 1 further comprises:
    a threaded set screw for attachment to internal threads of the rod holding element configured to hold a rod when tightened and a fastener driver tool to pass through the inner shaft to fasten and tighten the set screw.

3. The kit of claim 1 wherein the longitudinally extending grooves of the inner shaft are aligned with the edges of the inner shaft slots to allow the longitudinal rails of the outer shaft to slide relative to the inner shaft toward the distal end of the inner shaft.

4. The kit of claim 1 further comprising a locking knob rotationally coupled to a proximal end of the outer shaft wherein the inner shaft has one or more cam grooves and the locking knob is pinned to said cam groove causing the outer shaft to translate longitudinally upon rotation of the locking knob relative to the inner shaft toward an engaged position locking the pair of deflectable leg extensions in the coupled position to the rod holding element.

5. The kit of claim 4 wherein the one or more cam grooves has a cam over pocket feature in an end of the cam groove, wherein the cam over pocket feature locks the locking knob at or past the engaged position.

6. The kit of claim 5 wherein the cam over pocket at the end of the cam groove allows for rotational movement of the locking knob in the absence of longitudinal translation of the outer shaft relative to the inner shaft at the engaged position.

7. The kit of claim 1 wherein the inner shaft slots and the outer shaft slots are configured to align to allow the passage of a rod therethrough.

8. The kit of claim 1 wherein the rod reducer being comprises a hollow tube with a distal end to push a rod when placed over the inner and outer shaft.

9. The kit of claim 1 wherein the threads of the proximal end of the inner shaft have a pitch sufficient to allow the nut to auto-rotate, solely due to the weight of the nut, to abut the proximal end of the rod reducer, wherein further rotation of the nut pushes the rod reducer to move a rod.

10. The kit of claim 1 further comprising a locking knob, wherein the locking knob has flats configured to align with the flats of the outer shaft when the locking knob is rotated to a locked position allowing the rod reducer to non-rotationally translate as the nut pushes the rod reducer.

* * * * *